(12) United States Patent
Knebel et al.

(10) Patent No.: US 8,007,744 B2
(45) Date of Patent: Aug. 30, 2011

(54) SAMPLE CONTAINER FOR ANALYSES

(75) Inventors: Günther Knebel, Nürtingen (DE); Jörg Stappert, Kirchentellinsfurt (DE); Heinrich Jehle, Linsenhofen (DE); Joachim Kessler, Ulm (DE)

(73) Assignee: Greiner Bio-One GmbH, Frickenhausen (DE)

( * ) Notice: Subject to any disclaimer, the term of this patent is extended or adjusted under 35 U.S.C. 154(b) by 929 days.

(21) Appl. No.: 10/542,520

(22) PCT Filed: Jan. 16, 2004

(86) PCT No.: PCT/EP2004/000311
§ 371 (c)(1),
(2), (4) Date: Jul. 14, 2005

(87) PCT Pub. No.: WO2004/065009
PCT Pub. Date: Aug. 5, 2004

(65) Prior Publication Data
US 2006/0151322 A1    Jul. 13, 2006

(30) Foreign Application Priority Data

Jan. 17, 2003  (DE) .................................. 103 02 341
May 10, 2003  (DE) .................................. 103 21 042

(51) Int. Cl.
*B01L 3/00*    (2006.01)
(52) U.S. Cl. ..................... 422/547; 422/551; 422/552
(58) Field of Classification Search .................. 422/102, 422/104, 547, 551, 552
See application file for complete search history.

(56) References Cited

U.S. PATENT DOCUMENTS

| | | |
|---|---|---|
| 3,107,204 A | 10/1963 | Brown et al. |
| 3,649,464 A | 3/1972 | Freeman |
| 4,299,920 A | 11/1981 | Peters |
| 4,319,841 A | 3/1982 | Suovaniemi et al. |
| 4,493,815 A | 1/1985 | Fernwood et al. |
| 5,290,705 A | 3/1994 | Davis |
| 5,516,490 A | 5/1996 | Sanadi |
| 5,545,531 A | 8/1996 | Rava et al. |

(Continued)

FOREIGN PATENT DOCUMENTS

DE    29 02 026 A1    7/1980

(Continued)

OTHER PUBLICATIONS

Greiner Bio-One. Customer Drawing: AC 65500x. Jan. 12, 2005.*

(Continued)

*Primary Examiner* — Michael A Marcheschi
*Assistant Examiner* — Jameson Q Ma
(74) *Attorney, Agent, or Firm* — Vista IP Law Group LLP

(57) ABSTRACT

The present invention relates to a sample container for analyses suitable for medical diagnostics comprising a platform plate having at least one reaction chamber. The reaction chamber has a bottom and a sidewall which form a three-dimensional chamber which is open in the upward direction. The ratio of the numerical value of the surface area of the bottom is relatively large relative to the height of the sidewall. The ratio may be greater than or equal to 30, 35, 40, 45, 50, 60, 70, 80, or 90. The reaction chamber further comprises a binding area on an internal surface of the reaction chamber which may be functionalized for binding at least one chemical entity for use in an assay.

23 Claims, 9 Drawing Sheets

U.S. PATENT DOCUMENTS

| | | | |
|---|---|---|---|
| 5,728,350 A | 3/1998 | Kinoshita et al. | |
| 5,792,653 A | 8/1998 | Weibezahn et al. | |
| 5,840,256 A | 11/1998 | Demers et al. | |
| 5,891,630 A | 4/1999 | Eggers et al. | |
| 5,922,289 A | 7/1999 | Wong | |
| 5,948,673 A | 9/1999 | Cottingham | |
| 7,063,979 B2 * | 6/2006 | MacBeath et al. | 435/305.2 |
| 2002/0031449 A1 | 3/2002 | Loscher et al. | |
| 2003/0013130 A1 | 1/2003 | Charych et al. | |
| 2003/0092064 A1 * | 5/2003 | Reader | 435/7.1 |

FOREIGN PATENT DOCUMENTS

| | | |
|---|---|---|
| DE | 34 25 762 A1 | 2/1985 |
| DE | 3425 762 A1 | 2/1985 |
| DE | 33 36 738 A1 | 5/1985 |
| DE | 33 36738 A1 | 5/1985 |
| DE | 3336738 | 5/1985 |
| DE | 91 05 550 U1 | 8/1991 |
| DE | 91 07 670 U1 | 8/1991 |
| DE | 9105 550.4 | 8/1991 |
| DE | 91 07 670.6 | 9/1991 |
| DE | 41 32 379 A1 | 4/1993 |
| DE | 197 30 445 A1 | 1/1999 |
| DE | 692 28 291 T2 | 6/1999 |
| DE | 9692 28 291 T2 | 6/1999 |
| DE | 198 53 640 A1 | 6/2000 |
| DE | 199 04 784 A1 | 8/2000 |
| DE | 199 16 867 A | 10/2000 |
| DE | 299 23 461 U1 | 12/2000 |
| DE | 100 35 750 A1 | 2/2002 |
| DE | 100 49 902 | 4/2002 |
| DE | 100 49 902 A1 | 4/2002 |
| DE | 100 58 316 A1 | 6/2002 |
| DE | 101 05 711 A1 | 9/2002 |
| EP | 0 329 120 | 8/1989 |
| EP | 0 329 120 A2 | 8/1989 |
| EP | 0 454 046 A2 | 10/1991 |
| EP | 0 597 288 A1 | 5/1994 |
| EP | 0 816 828 A2 | 1/1998 |
| EP | 0816 828 A2 | 1/1998 |
| EP | 0 834 729 A2 | 4/1998 |
| EP | 0 976 453 B1 | 2/2000 |
| EP | 1 069 181 A2 | 1/2001 |
| EP | 1 110 611 A1 | 6/2001 |
| EP | 1 148 942 B1 | 10/2001 |
| EP | 1 148 942 B1 | 10/2002 |
| EP | 1 302 241 A2 | 4/2003 |
| EP | 0 976 453 B1 | 5/2004 |
| GB | 2 365 126 | 2/2002 |
| GB | 2 365 126 A | 2/2002 |
| WO | WO 82/02958 | 9/1982 |
| WO | WO 82/02958 A1 | 9/1982 |
| WO | WO 88/08789 | 11/1988 |
| WO | WO 88/08789 A1 | 11/1988 |
| WO | WO 95/23026 | 8/1995 |
| WO | WO 97/13839 | 4/1997 |
| WO | WO 98/23957 | 6/1998 |
| WO | WO 98/23957 A | 6/1998 |
| WO | WO 98/23957 A1 | 6/1998 |
| WO | WO 98/41323 | 9/1998 |
| WO | WO 98/45406 | 10/1998 |
| WO | WO 9855232 A1 * | 12/1998 |
| WO | WO 99/64157 | 12/1999 |
| WO | WO 00/16082 | 3/2000 |
| WO | WO 0242824 A | 6/2002 |
| WO | WO 02/057665 A2 | 7/2002 |
| WO | WO 02/063304 A3 | 8/2002 |
| WO | WO 02/077152 A1 | 10/2002 |
| WO | WO 2004/005477 A2 | 1/2004 |
| WO | WO 2004/065009 A1 | 8/2004 |

OTHER PUBLICATIONS

American National Standards Institute and Society for Biomolecular Sciences. "ANSI/SBS 1-2004". Jan. 2004. p. 1-8.*
English Translation of Preliminary Report on Patentability for PCT/EP2004/000311, pp. 1-4, Dec. 1, 2005.
STN Easy English Translation of Abstract of DE 197 30 445 A1, p. 1, Mar. 2, 1999.
eScience Abstract of WO 2002242824, p. 1, Jul. 30, 1993.
STN Easy English Translation of Abstract of DE 33 36 738 A1, p. 1, Sep. 25, 1993.
STN Easy English Translation of Abstract of DE 10049 902 A1, p. 1, Oct. 10, 2000.

* cited by examiner

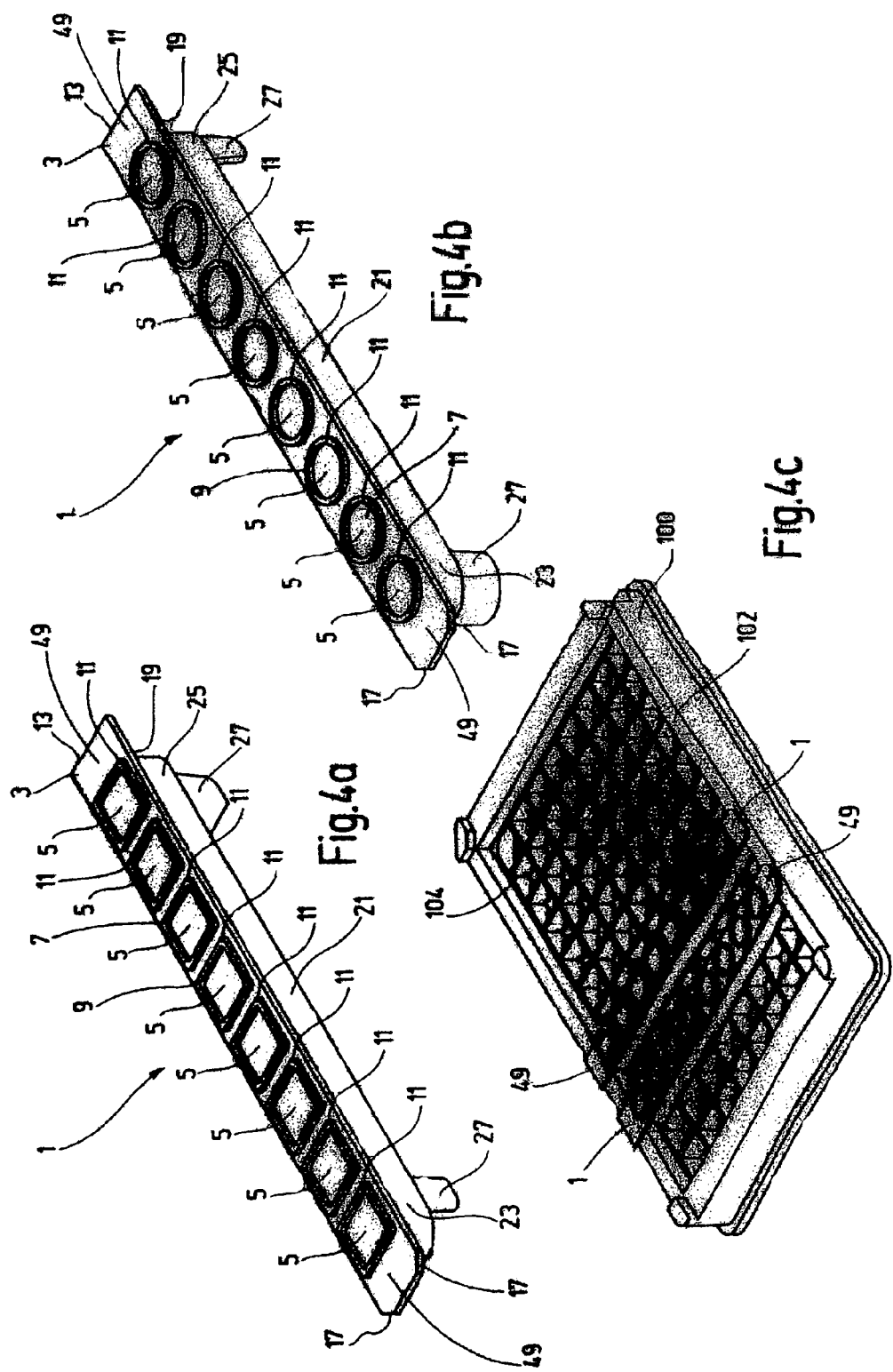

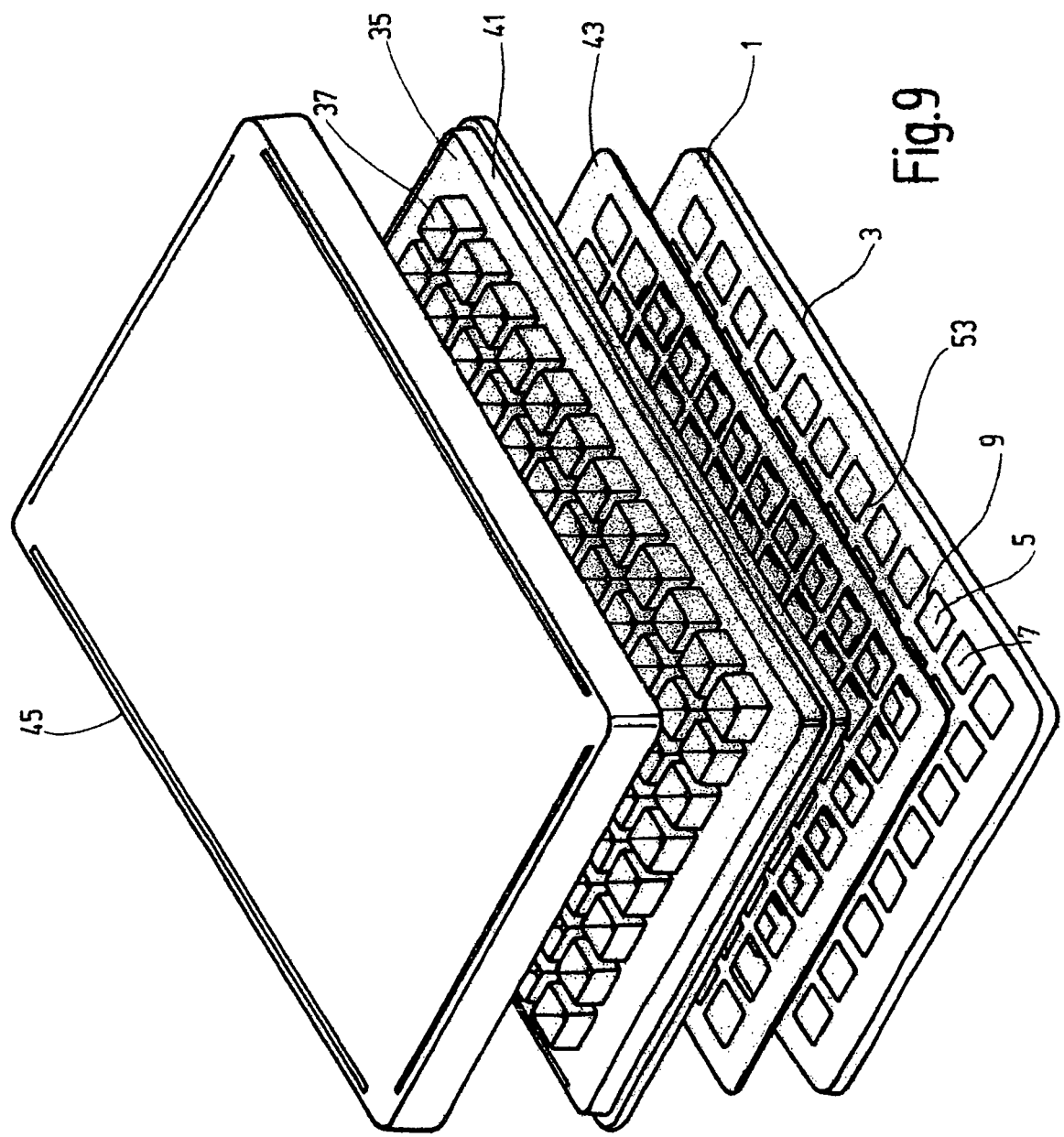

US 8,007,744 B2

SAMPLE CONTAINER FOR ANALYSES

RELATED APPLICATIONS

This application is a U.S. National Stage filing under 35 U.S.C. §371 of International Application No. PCT/EP2004/000311, filed Jan. 16, 2004, which claims priority to German Patent Application No. 103 02 341.0, filed Jan. 17, 2003, and also claims priority to German Patent Application No. 103 21 042.3, filed May 10, 2003. The contents of the aforementioned applications are hereby incorporated herein by reference in their entireties. Priority to the aforementioned applications is hereby expressly claimed in accordance with 35U.S.C. §§ 119, 120, 365 and 371 and any other applicable statutes.

FIELD OF THE INVENTION

The present invention relates to a sample container for analyses, specifically a biochip platform comprising a platform plate having at least one reaction chamber (compartment) that is suitable for use in medical diagnostics or for screening for pharmaceutically active compounds.

BACKGROUND OF THE INVENTION

Microplates for the titration of biological or chemical materials or for performing measurements of fluorescence, luminescence, or other measurements are known in the art. Microplates in the form of multicuvettes are used specifically in research, and in clinical and industrial applications, for example to perform blood group serology, antibiotics test series, complement titrations, and other laboratory work in which, for example, geometric dilution series are necessary. The standard size for biochemical and cellular biological tests is a microtiter plate having 96 wells ("sample wells" or depressions) with a reaction volume of up to 500 μl per well. There is a growing trend to use microtiter plates having 384 wells or even 1536 wells. This trend to increasing miniaturization is mainly being driven by combinatorial chemistry and by HTS (high-throughput screening). Both areas are currently among the pillars of screening for modern pharmaceutically active chemical compounds.

HTS is used, for example, to determine whether an active ingredient that can be used as the basis for new medications is present in a substance (chemical compound) library. The components of the substance library are studied in the test procedure to determine their reactivity with a target (target molecule). Substances that are identified in the test procedure are possible candidates as an active ingredient that can affect the function of the respective target molecule. The active substances are detected by means of optical methods such as absorption, fluorescence, luminescence, or by detecting radioactivity by means of scintillation. The large number of interactions being tested results in a high level of variance in the test systems and the associated detection modes.

Active ingredient screening requires that the targets that are responsible for causing diseases first be found. As a consequence of the growing body of knowledge in modern molecular biology, more and more disease-causing or disease-influencing genes are being identified. These genes can then be acted upon using suitable medications. Miniaturized carriers, so-called biochips, represent a milestone in the analysis of biologically active molecules, in particular for the identification of the genes that are responsible for causing diseases. Biologically active molecules having a known composition can be immobilized or synthesized across the full surface of such carriers or in a structured array. The immobilized biological molecules may, for example, be nucleic acids or fragments of nucleic acids, or proteins or fragments of proteins. For example, the nucleic acid determination in samples that are to be tested can be significantly simplified, accelerated, parallelized, automated, and made more precise with the help of biochips containing immobilized nucleic acid. Such biochips are also referred to as DNA chips or DNA arrays. DNA chips or DNA arrays are used, for example, in the clinical diagnosis of infectious, cancerous, and genetic diseases. The efficiency of such DNA chips in the analysis of samples is based in particular on the fact that only small sample volumes are needed, and the evaluation can be performed using highly sensitive test methods. Thus, large numbers of samples can be tested quickly using such chips. Protein arrays are also known. In them, proteins or peptides are arranged in a structured and known array in a manner similar to that employed with DNA chips, for example on plastic membranes. Such protein arrays are mainly used to study the interactive binding of proteins—for example, a receptor-ligand interaction—in order to identify intracellular protein complexes, to study DNA protein and RNA protein interactions, or to analyze protein-antibody interactions. With the help of protein chip technology, researchers have already been able to identify numerous protein markers for cancerous diseases and for diseases like Alzheimer's disease.

The miniaturization of microplate test systems has numerous advantages on the cost side, but it is also associated with major problems in technical implementation. As a result of this miniaturization of microtiter plates, the tests to be performed in the wells must also be miniaturized to an ever greater extent. Therefore, stricter specifications are also being established for the detection devices, with increasingly smaller volumes being used. It is known that specific problems occur with extremely small volumes in individual detection types. For example, in the case of luminescence measurement, a low sample volume also means a smaller signal for optical detection, which adversely affects the sensitivity of the measurement. The measurement of absorption is mainly disrupted by the meniscus effect that occurs at the surface of the liquid, since the shape of the meniscus is highly variable in extremely small sample chambers. The only measurement that is not influenced by volume is the measurement of fluorescence. Here too, however, the sensitivity that is achievable is limited by the inherent fluorescence of the plastic material used in the microtiter plates, since in most processes this inherent fluorescence affects the fluorescent measurment.

In particular, problems are encountered with microplates that have several hundred wells. Since the opening of such wells must be very small and, moreover, since it is frequently delineated by annular beads, while at the same time the volume is relatively high, the detection systems used to detect the reactions in the wells, for example scanner devices, cannot be arranged perpendicularly at an optimal angle of 90° over or in the opening in the wells, but rather they must be positioned at an acute angle above the openings or within the openings, whereby the angle in some cases is substantially less than 90°. This results in a shadow effect, which also corrupts the analytical results obtained by means of the detection systems. For spotter devices, which are used to coat the bottoms of the wells with, for example, nucleic acids, there are technical problems, since the spotters must be inserted relatively deep into the wells.

In pharmaceutical research, or in basic research, the problems encountered with microtiter plates with regard to miniaturization can frequently be tolerated. Here the primary goal is to subject a large number of samples to the same test procedures in parallel batches on a single plate. Therefore, it is often fully adequate to detect the difference in the signal intensity between the individual wells and thereby to obtain more of a qualitative analysis. However the situation is completely different in clinical diagnostics. Here, for example, it is very frequently the case that samples, for example body fluids, from a single patient must be subjected to various test procedures using different reactants, whereby each test can involve using comparatively few reaction mixtures. On the other hand, it is also often necessary to test a large number of samples from various patients for a single parameter. In contrast to high-throughput screening, here the individual clinical tests have to permit reliable quantitative conclusions in order, for example, to be able to detect the onset of a disease or trace the progress of a disease in an individual patient. The problems that occur with the detection systems in extremely small volumes therefore can result in serious errors in the resulting test data used in clinical diagnostics. Thus, the accuracy of detection plays a much larger role in clinical diagnostics than it does, for example, in high-throughput screening of active ingredients.

The basic technological problem that underlies the present invention is to provide an analysis sample container, in particular one for patient-specific clinical and chemical tests, that can be used in particular as a biochip after biologically active molecules have been immobilized and that overcomes the disadvantages known in the prior art and permits clinical parameters to be determined quickly and reliably, whereby in particular it is possible to detect relevant clinical/chemical parameters quantitatively and free of errors utilizing automated detection technology.

SUMMARY OF THE INVENTION

The present invention solves the underlying technical problem by providing a biochip (microarray) platform comprising a platform plate having at least one three-dimensional reaction chamber, whereby the reaction chamber and the volume of the reaction chamber, which is open facing upward, is defined by laterally enclosing side walls, whereby the ratio of the surface area of the bottom to the height of the side walls is greater than or equal to 30, preferably greater than 50. The bottom and/or at least one side wall of at least one reaction chamber is embodied as a binding matrix having a functional group that makes it possible to bind a natural or synthetic molecule, in particular a biologically active molecule.

More particularly, in the present invention the ratio of the numerical value of the surface area of the bottom, which is expressed in $mm^2$, to the numerical value of the height of the side walls, which is expressed in mm, measured at the lowest part of the preferably flat bottom to the upper edge of the side wall, preferably is greater than or equal to 30, 35, 40, 45, 50, 60, 70, 80, or 90. Preferably, the ratio of the numerical value of the bottom surface area to the numerical value of the height of the side walls is 30 to 100, and more preferably between 32 and 80. Even more preferably, the ratio of the magnitude of the bottom surface area to the height of the side walls is greater than or equal to 50. In addition, it is preferable in actual experience that the upper edges of the side walls of the reaction chamber form the highest part of the biochip platform.

The biochip platform of the invention therefore comprises a platform plate and at least one three-dimensional reaction chamber, and the reaction chamber is constructed of a bottom and side walls which laterally encompass the volume of the reaction chamber and close it off, and the reaction chamber has an opening in the upward direction, preferably with the same surface area and geometry as the bottom, and the ratio between the surface area (S) of the bottom and the height of the side walls, which is described above, preferably is greater than or equal to 30, preferably greater than 50.

The present invention therefore provides a biochip platform on which at least one, however in other preferred embodiments a plurality of, reaction chambers or cavities, is/are disposed, and the reaction chamber or the reaction chambers have a relatively large bottom surface area relative to their height. In the prior-art microplate systems, the ratio between the surface area of the bottom of the cavity and its height is less than 5 and therefore is substantially less than that in the biochip platform of the present invention.

The substantially increased ratio between the surface area of the bottom of the reaction chamber and the height of the side walls that is provided for in the present invention has the advantage that, even though the volume of the reaction chamber is small, a large surface is provided that has numerous binding sites in order to immobilize biologically active molecules and therefore to perform reactions. In addition, the reaction chamber of the invention permits a substantially improved evaluation of the tests performed in the reaction chamber using conventional detection systems, since the sources of errors caused by the dimensions of conventional wells, which tend to distort the measurement values, are eliminated. Because of their low depth, the reaction chambers of the invention permit a conventional scanner or some other conventional detection device to be positioned vertically over or vertically within the opening in the reaction chamber at an angle of 90° and then to perform the corresponding measurement. In contrast to conventional microtiter plates, this means that there are no shadowing effects, which could result in errors in the acquired measurement values. Because of their low depth, the reaction chambers of the biochip platform of the invention also make it possible, for example, to easily apply a nucleic acid to the bottoms of the individual reaction chambers using a conventional spotter, without having to insert the spotter very deeply into a reaction chamber.

In contrast to conventional biochips, in which biological molecules are applied to a planar level platform, in particular a glass platform, in the form of spots, and in which no defined reaction chambers or separate reaction chambers are present, the biochip platform of the invention is compartmentalized in the form of at least one single defined reaction chamber or in other embodiments a plurality or a large number of separate reaction chambers. The biochip platform therefore can also be used for reactions with reactants that are exclusively in solution, and in which, as needed, different reactions can be performed with different reactants. Furthermore, the biochip carriers of the invention can also be used to perform reactions in which at least one reactant is bonded to the surface of the bottom of the reaction chamber. In contrast to conventional biochips, because of the compartmentalization of the biochip platform of the invention, different reactions with the same or different bonded reactants can be performed as needed in the individual reaction chambers of the biochip platform of the invention. Since the reaction chambers of the biochip platform of the invention are embodied as separate cavities, it is possible, for example, in the individual reaction chambers of a biochip platform of the invention to simultaneously perform different nucleic acid hybridizations with different nucleic acids and/or different protein-protein binding reactions with different proteins, without these individual reactions interfering with each other. In contrast to the biochip platform of the invention, a conventional, non-compartmentalized biochip does not afford this opportunity. Thus, the biochip platform of the present invention advantageously combines the advantages of chip technology with the advantages of microtiter plate technology.

The biochip platform of the invention is especially suitable for performing patient-specific nucleic acid analyses or protein analyses. It is provided for in the invention, for example, that the bottom surface of the reaction chambers of the biochip carrier of the present invention is functionalized with chemical groups that permit a binding of biological molecules, in particular of nucleic acid probes having a known nucleic acid sequence or with proteins having a known amino acid sequence. By immobilizing biologically active molecules and using the biochip platform of the invention having functionalized reaction chambers, it is possible to produce a biochip which, for example, permits a multitude of diagnostic nucleic acid hybridizations or nucleic acid protein binding reactions or protein-protein binding reactions to occur.

Moreover, the invention provides that in one embodiment of the invention, the biochip platform of the invention has dimensions that permit the biochip platform of the invention to be inserted into a conventional microtiter plate having standard SBS (Society of Bimolecular Screening) dimensions. In one embodiment the biochip platform of the invention is constructed in the form of a strip whose length permits insertion into a microtiter plate that complies with the SBS standards, while the width of the strip may be varied. The strip configuration of the biochip of the invention is extremely advantageous, particularly in clinical diagnostics, for example for acquiring the clinical chemical parameters of an individual patient. The reaction chambers can be arranged linearly in rows on a strip, and a plurality of rows can be arranged next to each other on each strip.

In clinical diagnostics, for example, various samples, such as various body fluids from an individual patient, must be subjected to a large number of different clinical/chemical tests. These various tests may differ from each other significantly with respect to their processing steps as well as with respect to the required test conditions, for example with respect to the necessary temperature range or temperature profile. It is frequently the case that the only common characteristic of these tests is that the same sample, for example a body fluid, must be analyzed in a limited number of parallel tests. The biochip platform of the invention, which, for example, is configured as a strip, may—for example, depending on the number of tests to be performed—have at least one reaction chamber, however preferably a plurality of reaction chambers, for example 2, 3, 4, 5, 6, 7, 8 or more reaction chambers arranged, for example, in rows. In the invention, the biochip platform of the invention that is constructed in strip form may have $2^n$ reaction chambers with $n \geq 0$, for example 2, 4, 8, or 16 reaction chambers. This number of reaction chambers on a biochip platform of the invention is generally adequate to perform, for example, an individual patient-specific test with corresponding controls and parallel reaction mixtures. If in a different preferred embodiment the biochip platform is constructed in the shape of a rectangular microtiter plate, for example in the SBS standard format, a total of from 1 to, for example, 1536, preferably 1, 12, 24, 36, 48, 96 or additional multiples of 8 or 12 reaction chambers may be present, preferably in the form of a matrix. The biochip platform can also be configured in the form of a matrix so that it has dimensions that permit it to be inserted into a microtiter plate complying with the SBS standard. This matrix-shaped biochip platform has, in its preferred embodiment, length and width dimensions that essentially correspond to a microtiter plate, so that the biochip platform can be placed on, clipped onto or clipped into the conventional microtiter plate, either completely or partially, preferably in a removable manner, covering said microtiter plate completely or essentially completely on the upward-facing side.

Various individual patient-specific tests may be conducted in an advantageous manner on various biochip carriers of the invention or biochips that are produced using various biochip carriers of the invention. The biochip carriers or biochips used to conduct various clinical tests may differ, for example, in that different nucleic acids or proteins are immobilized in their cavities. The various biochip carriers or biochips used for the diagnosis of an individual patient, for example constructed in a strip shape, that are to be used for individual tests can be inserted, in accordance with the invention, into the same microtiter plate using suitable pipetting techniques in order to apply the same sample from an individual patient simultaneously onto all of the biochip carriers or biochips. After the sample from this individual patient is applied, the biochip carriers or biochips used to perform specific tests can be combined with corresponding biochip carriers or biochips that have samples from other individual patients on other microtiter plates, so that these biochips can simultaneously be subjected to the same test process steps or the same test conditions. After successful completion of the test, the corresponding individual patient-specific biochip carriers or biochips can again be combined on a separate microtiter plate and together they can be evaluated using a single detection system. The strip-shape of the biochip platform of the invention therefore permits a high degree of flexibility in specimen processing and evaluation.

In conjunction with the present invention, a "biochip" is understood to be a device that comprises a platform having at least one cavity or reaction chamber in which biologically active molecules, for example nucleic acids or proteins, are immobilized or fixed and with whose help, for example by means of hybridization and/or binding processes, a small amount of a ligand that can bind to these biologically active molecules under suitable conditions, can also be detected in a small sample. The biochip may be used as a chip module, reaction module, test module, test device, analysis module, analysis chamber, or analysis device.

In conjunction with the present invention, a "biochip platform" is understood to mean a device that comprises a platform plate having at least one cavity or reaction chamber in which biologically active molecules such as nucleic acids or proteins can be immobilized or fixed. The biochip platform can therefore be used to produce a biochip by immobilizing or fixing biologically active molecules in the reaction chamber, in particular on the functionalized surface of the bottom of the reaction chamber.

The "platform plate" of the biochip platform is understood to mean a thin, flat element, preferably having a rectangular shape that is made of a metal, a metal oxide, a plastic, a membrane, glass, ceramic, or a hybrid or combination thereof. In conjunction with the invention this means that the platform plate of the biochip platform of the invention is completely comprised of one of the above materials or contains substantial amounts thereof, or is completely comprised of a combination of these materials or essentially comprises these materials, or that the surface of the platform plate of the biochip platform of the invention consists completely of one of the aforesaid materials or that it essentially contains them or that it completely contains a combination of these materials or that it essentially contains said combination. The platform plate or its surface nearby comprises at least 50%, 60%, preferably approximately 70%, more preferably approximately 80% and most preferably approximately 100% of one of the aforesaid materials or the combination of said materials. In a preferred embodiment, the platform plate of the biochip platform of the invention comprises approximately 100% plastic. The platform plate is the platform of at least one reaction chamber, and it makes it possible to handle this reaction chamber, in other words it functions as a frame or holder. In a preferred embodiment the platform plate has contact surfaces and/or fastening means, for example detent devices, plug-in devices, or other devices that permit the completely reversible placement, plugging, connecting or clipping of the microchip platform onto or into a conventional microtiter plate, where the biochip platform completely or partially covers the cavities of the microtiter plate in an upward direction. The reaction chamber, of which at least one is present, can be constructed on or in the platform surface. The reaction chamber, of which at least one is present, may therefore be constructed in an integral manner, in other words it is made of a single piece with the platform plate, however in a different embodiment it can be placed onto the platform piece as a separate unit and reversibly or irreversibly connected to it. The reaction chamber, of which at least one is present, may accordingly consist or be comprised of the materials that were described above for the platform plate.

A "reaction chamber" or "cavity" is understood to mean a geometrical body consisting of the bottom and the side walls that laterally define the bottom, and an opening that is formed by the upper edge of the side walls. Thus, a "reaction chamber" or "cavity" is understood to mean a geometrical structure comprising a bottom and side walls; the bottom and the side walls are disposed relative to each other in such a way that they enclose a volume in the downward and lateral directions, and the thus encompassed volume has an opening facing upward. The side walls may be constructed as an embankment, wall, web, protrusion, bead, or annular bead. Thus, the reaction chamber surrounds in the downward direction and laterally, with an opening facing upward, a volume within which biochemical reactions, in particular nucleic acid hybridizations, DNA-protein binding reactions, protein-protein binding reactions, etc. may be performed. The invention provides that the bottom of the reaction chamber represents a flat planar surface, and the bottom of the reaction chamber seen in a plane view in particular has the shape of a circle, rectangle, square, hexagon, polygon, or an ellipse, in accordance with the invention. The side walls of the reaction chamber preferably have the same height. All of the side walls preferably are disposed perpendicular to the bottom, however embodiments of this invention may also have deviating angles between the side wall and the bottom.

An especially preferred embodiment of the invention relates to a biochip platform in which the upper edge of the side walls of the reaction chamber represents the highest part of the biochip platform of the invention. In combination with the present invention, the "upper edge of the reaction chamber" is the uppermost point—in other words the highest point—of the reaction chamber, which is defined by the side walls of the reaction chamber. The invention provides that the upper edges of at least two, preferably of all of the reaction chambers of a biochip platform are at the same height.

An especially preferred embodiment of the invention relates to a biochip platform in which the upper edge reaction chamber lies in a plane above the upper edge of the platform plate of the biochip platform. In conjunction with the present invention the "upper edge of the platform plate" which is oriented upward, in other words in the same direction as the opening of the reaction chamber, is understood to mean the uppermost area of the platform plate, in particular an area that essentially extends across the same height of the entire platform plate and can also be characterized as its surface.

In a preferred embodiment the bottom of the reaction chamber is formed by the platform plate, while the side walls of the reaction chamber are constructed for example as raised areas on the platform plate, and in a preferred embodiment the shape of the bottom may, for example, be square, polygonal, hexagonal, elliptic, rectangular, or circular. In a preferred embodiment the bottom lies in the same plane as the surface of the platform plate. The side walls of the reaction chamber, which are formed for example as raised areas, may for example be present in the form of annular beads or an annular wall, in other words the upper edge of the reaction chamber extends about the circumference of the reaction chamber and is separated from the annular bead or the annular wall of the next reaction chamber by means of a depression. In this embodiment the upper edge of the reaction chamber then represents the uppermost area of the annular bead.

In another embodiment of the present invention in which the side walls are formed by raised areas and the upper edge of the side walls lies above the upper edge of the platform surface, the biochip platform is designed in such a way that the reaction chamber, of which at least one must be present, is located on a base, pedestal, or a raised area on the platform plate. In a preferred embodiment the outline of the base conforms to the outline of the bottom of the respective reaction chamber. An embodiment of this type therefore comprises a platform plate, on which at least one reaction chamber disposed on a base is located. The preferably flat, planar surface of the bottom accordingly is located above the upper edge of the platform plate at a vertical distance that corresponds to the height of the base. It is preferred for each reaction chamber in the biochip platform that a separate base be provided, so that the number of bases corresponds to the number of reaction chambers. The design of the reaction chamber itself, in particular the ratio of the basic surface area of the bottom and the height of the side walls as well as the geometric design of the side walls of the basic contour of the reaction chamber, etc. is described above as for the other embodiments.

In a further preferred embodiment the invention provides a biochip platform in which the upper edge of the reaction chamber and the upper edge of the platform plate lie in the same plane and the bottom is disposed below the upper edge of the platform plate. In other words, the invention provides that the reaction chamber is disposed within and/or below the platform plate as a depression, and in effect is recessed into the platform plate, and the opening of the reaction chamber is closed off by the upper edge of the platform plate, without the opening of the reaction chamber being surrounded by side walls configured as a raised area, for example, by an annular bead or an annular wall. In this embodiment the height of the vertical side walls corresponds to the distance between the preferably flat bottom and the upper edge of the platform plate. In this embodiment the side walls are formed by the platform plate.

Of course, the reaction chamber can also be only partially sunk into the platform plate, so that the bottom does lie below the upper edge of the platform plate, the lower part of the side walls is formed by the base plate, and above the platform plate the side walls extend with a lengthening of the side wall components out of the recess above the upper edge of the recess. The upper edge of the side wall then lies above the upper edge of the platform plate so that in this embodiment the side walls are also configured as raised areas.

In a preferred embodiment of the invention, the biochip platform of the invention has, as already explained, dimensions that make it possible to insert the biochip platform with a precise fit into a microtiter plate having the standard SBS dimensions (Society of Bimolecular Screening). If the biochip platform has the exact, or substantially exact, dimensions of a microtiter plate complying with the SBS standard, then it is provided according to the invention that the number of reaction chambers on the platform plate be at least 1, 4, 8, 12, or integer multiples of 8 or 12.

The invention provides that the biochip platform of the invention may be preferably configured as a strip. In an especially preferred embodiment of the invention, the biochip platform of the invention has dimensions of approximately 75×25 mm (length×width, the term "length" as used herein means: the larger dimension in the plane of the matrix or the strip, and the term "width" as used herein means: the smaller dimension in the aforesaid plane). If the biochip platform of the invention has these dimensions, it is provided in accordance with the invention that at least one but also two parallel rows of reaction chambers are disposed on the platform plate, and each row comprises at least one, however also two or more, for example eight, reaction chambers arranged at a given distance one after another.

In another preferred embodiment of the invention, the biochip platform according to the present invention is in a strip shape having a width of 9 mm. The length of the strip is preferably selected in such a way that it permits the biochip platform to be inserted into a standard microtiter plate (SBS), preferably in such a way that the length of the strip is arranged perpendicular to the length of the standard microtiter plate. It is provided in accordance with the invention that a series of eight reaction chambers arranged in a row at a distance from one another is disposed on the biochip platform of the invention that has this dimension.

In an especially preferred embodiment of the invention, the biochip platform in the form of a strip having the dimensions of approximately 75×25 mm and on the biochip platform having a width of 9 mm, the reaction chambers have a circular base area having a diameter of 6 mm and a standard height of 0.5 mm. The ratio of the numerical value of the bottom surface area to the numerical value of the height of the side walls is approximately 56 in this embodiment of the reaction chamber. In a further especially preferred embodiment of the invention, the reaction chambers arranged in the biochip platform that is designed in a strip shape may have a square bottom surface with a side length of 6 mm and a side wall height of 0.5 mm. In this embodiment, the ratio of the numerical value of the bottom surface area to the numerical value of the height of the side walls is 72.

In accordance with the invention, a preferred embodiment provides that the platform plate and the reaction chambers of the biochip platform of the invention are constructed in a single piece, and that the reaction chambers are an integral component of the platform plate. The biochip platform preferably comprises plastic. The plastic used to manufacture the biochip more preferably is cycloolefin copolymer (COC), cycloolefin polymer (COP), acrylobutadiene styrene, polyamide, polycarbonate, polyester, polymethylmethacrylate, polypropylene, polystyrene, SMA (styrene-maleic acid anhydride copolymer), or styrene acrylonitrile.

In accordance with the invention, the bottom of the reaction chamber, of which at least one is present, is constructed as a binding matrix with a functional group that permits the binding of a natural or synthetic molecule, in particular a biologically active molecule. In a preferred embodiment, the bottom of the reaction chamber that is designed as the binding matrix is comprised of glass, a polymer, a membrane, or a hybrid thereof, and at least one functional group that, for example, can immobilize a natural or synthetic molecule, in particular a biologically active molecule, on the surface of the bottom by means of covalent bonding or also through a Brönstedt acid-base interaction. The bottom of the reaction chamber is therefore, in accordance with the invention, a bonding matrix having a functional chemical group that permits binding, in particular covalent bonding, to a complementary group of a natural or synthetic molecule, in particular a biologically active molecule. In conjunction with the present invention, the term "functional group" is understood to mean a chemical group that is applied to the bottom of the reaction chamber and that is able to interact with a natural or synthetic molecule that is to be immobilized, in particular with a biologically active molecule, in such a way that, in particular, covalent or ionic bonding can take place between the two bonding partners.

In a preferred embodiment the bottom of the reaction chamber is comprised of a polymer that has at least one functional group on the surface.

The functionalization of the surface, in particular of the surface of a polymer may, in accordance with the invention, be accomplished using chemical functionalization processes, plasma functionalization processes, UV functionalization processes, or using graft co-polymers.

A preferred embodiment of the invention therefore relates to a biochip platform in which the functional group is applied to the surface of the polymer using a chemical functionalization process.

If the bottom surface of the reaction chamber is comprised of a polymer that has aromatic substituents, for example phenyl groups, as is the case with polystyrene, a chloromethyl spacer can be applied to the polymer by means of 1-chlorodimethylether in the presence of a Lewis acid, for example $AlCl_3$, by means of an electrophilic aromatic substitution of the aromatic components. The resulting chloromethyl compound is activated with respect to nucleophilic reagents to attach carbon-element bonds accompanied by the release of chloride. The chloromethyl compound can then be substituted further, and the substitution can be accomplished by means of N-nucleophiles, for example $NH_3$, or O-nucleophiles. By selecting a suitable nucleophile, such as HO-aryl-CHO or formylacetic acid $HO(O)C—CH_2—CHO$, an aldehyde function may be introduced directly. A further option for covalent bonding is provided by amide bonding. The surface-fixed carboxylic acid required for this can be obtained by the reaction of dicarboxylic acids with chloromethyl-functionalized polystyrene. In this way, one acid compound is fixed on the surface, while the second compound can be used to bond with the target molecule, or in other words, the biological molecule that is to be bonded. The remaining C(O)OH compound can then be activated by converting it into the corresponding acid chloride. However, one problem here is the unstable compound, which is to be reacted further in situ. However, the covalent bonding of the acid compound to the amine is possible without previous activation.

A preferred embodiment of the invention therefore relates to a biochip platform in which the polymer of the bottom is a polymer having aromatic substituents on whose surface chloromethyl groups are located. The polymer having aromatic substituents is preferably polystyrene.

A further preferred embodiment of the invention relates to a biochip platform in which the bottom of the reaction chamber comprises a polymer that has at least one derivatized chloromethyl compound on its surface, and the chloromethyl group is substituted by an aldehyde group, by an amine compound, or by a carboxylic acid.

With a saturated polymer, for example TOPAS (cycloolefin copolymer, norbornene basic structure; manufactured by Ticona Frankfurt, Germany), it is not possible to introduce a $CH_2Cl$ function since no aromatic ligands are present. Saturated polymers however can be chlorinated by means of free-radical chlorination using a catalyst. The resulting carbon-chlorine units can also be derivatized.

A preferred embodiment of the invention therefore relates to a biochip platform in which the bottom of the reaction chamber comprises a saturated polymer whose surface is chlorinated. The saturated chlorinate polymer is preferably chlorinated TOPAS.

A further preferred embodiment of the invention relates to a biochip platform in which the functional group is applied to the surface of the polymer that forms the bottom of the reaction chamber using a plasma functionalization process.

In accordance with the invention, a surface functionalization using a plasma process therefore can also be used. Atmospheric oxygen plasma generates free radicals and a wide range of ions, and in particular oxygen functionalities are formed on the surface of the polymer. Because of the very high excitation energy and the extremely harsh conditions, carbon bonds on the surface of the polymer are broken and various carbon-oxygen functionalities are formed. While C—O single bonds are inactive relative to covalent bonds, carboxylic acid functions are active relative to a covalent amide bond. Aldehydes can immobilize amino-modified biological molecules to form a Schiff base.

By suitably modifying the reaction conditions, amine functions can be formed on the polymer surface by means of plasma functionalization processes. The amine functions produced in this manner may already be used for the covalent bonding of carboxyl groups. There are two ways that reactions can be used to do this, namely, the amide bonding of terminal —C(O)OH acid compounds and the imine bonding from the existing internal C=O double bonds. In addition, plasma-treated polymer surfaces can be derivatized without difficulty. For example, aminated surfaces can be re-functionalized to form surfaces that have aldehyde functions, where at the same time the distance between the functional groups and the surface of the polymer can be increased. Oxygen-containing surfaces can be subjected to a carboxylic acid derivitization and then to the installation of a spacer to obtain the aldehyde function.

The present invention also relates to biochip platforms obtained by using plasma processes, wherein the surface has carboxylic acid, aldehyde/ketone, amine, epoxy, and/or halogen functions.

A further preferred embodiment relates to biochip platforms in which the functional group is applied to the surface of the polymer that forms the bottom of the reaction chamber by using photo-induced surface functionalization.

The process of photo-induced surface functionalization is also suitable for applying functional groups on the polymer surface. In particular, the anthraquinone process can be used for this purpose. In it, the functional group needed for the covalent bonding of the biological molecule is bound by means of a chemical linking reaction to an anthraquinone derivative. However, strong donors, for example OH, OMe, or $SO_3H$, are needed on the anthraquinone frame for this coupling step. Further possible ways to achieve anthraquinone derivatization result from the use of Aldrich 16,554-9 ($C_{14}H_9O_2N$), Aldrich 43,425-6, or Aldrich 25,272-7. The entire unit is then photochemically fixed on the polymer frame by means of a free-radical mechanism.

A further photo-induced surface functionalization process is photochemical grafting, in which variable base materials are produced by controlled reactive coatings with polymers that can carry various functional groups. The reaction is initiated photochemically, in particular using UV light.

The present invention therefore also relates to a biochip platform in which the functional group is applied to the polymer surface by reacting anthraquinone with a donor, followed by photochemical fixation. The present invention also relates to a biochip platform in which the functional group is applied to the polymer surface by means of photochemical grafting.

A further preferred embodiment relates to a biochip platform in which the functional group is applied to the surface of the polymer that forms the bottom of the reaction chamber by using graft polymerization.

Non-polar matrix polymers, for example polypropylene, polyester, or EPM (ethylene-propylene monomer elastomer) can also be functionalized by grafting on monomer substances having polar groups using a twin-screw kneader. Such graft copolymers can be used as the starting components for manufacturing polymer blends and polymer alloys. In this way, polypropylene/polyamide alloys, for example, or thermoplastic elastomers (pp/EP(D)M blends; polypropylene/EPM blend) can be produced using a dynamic cross linking of the elastomer phase.

A further preferred embodiment of the invention relates to a biochip platform, or a biochip produced using the biochip platform of the invention, in which a natural or synthetic molecule, in particular a biological molecule, or a biologically active molecule is bonded on the bottom of the reaction chamber. In conjunction with the present invention, this is a "natural molecule"—a molecule that is preferably isolated from a natural source or a natural material, and, after being isolated, might have been subjected to one or more transformations, modifications, and/or chemical derivatizations. A "synthetic molecule" is specifically understood to mean a molecule produced by synthetic means. Preferably, the natural or synthetic molecule has a biological activity—in other words it is a biologically active molecule. If the natural or synthetic molecule itself does not have any biological activity, it at least is capable of bonding a biologically active molecule or forming an association with it and thereby immobilizing the biologically active molecule on the surface of the bottom.

The biological molecule, respectively the biologically active molecule is, in particular, a protein, a nucleic acid, or a PNA molecule.

In accordance with the invention, the biologically active molecule or biomolecule is immobilized or bound or can be immobilized on the base surface of the reaction chamber after it obtains its biological activity. The "biological activity" of the biologically active molecule or biomolecule is understood to mean all functions that this molecule performs in its natural cellular environment in an organism. If the molecule is a protein, these may be specific catalytic or enzymatic functions, functions used in immune defense mechanisms, transport and storage functions, regulation functions, transcription and translation functions, etc. If the biological molecule is a nucleic acid, the biological function may, for example, involve coding a gene product or using the nucleic acid as a template for synthesizing additional nucleic acid molecules or as a bonding motif for regulatory proteins. "Maintaining the biological activity" means that, after a biologically active molecule has been immobilized or bound on the polymer surface, in other words on the bottom of the reaction chamber of the biochip platform of the invention, the same or nearly the same biological functions can be exercised to at least the same extent as the same molecule would be able to do in a nonimmobilized state under suitable in-vitro conditions, or the same molecule would be able to do in its natural cellular environment. In regard to the present invention, the term "immobilization" means that a molecule is bound in this way to the functional groups of the polymer surface, or for example that the three-dimensional structure of the domain(s) necessary for the biological activity is/are not changed relative to the non-immobilized state, and that these domain(s), for example bonding pockets for cellular reaction partners is/are freely accessible to native cellular reaction partners when they come in contact with these reaction partners.

In accordance with the invention, the biological molecule that is immobilized or can be immobilized on the biochip platform of the invention is in particular a nucleic acid, a protein, a PNA molecule, a fragment thereof, or a mixture.

In conjunction with the present invention, a "nucleic acid" is understood to be a molecule that consists of at least two nucleotides connected together by means of a phosphorus di-ester bond. The nucleic acids may either be a deoxyribonucleic acid or a ribonucleic acid. The nucleic acid can be present in both single-strand and double-strand form. In the context of the present invention, a nucleic acid can also be an oligonucleotide. The nucleic acid that is bound to the base surface of the reaction chamber of the biochip platform of the invention preferably has a length of at least 10 bases. In accordance with the invention, the bound nucleic acid may be of natural or synthetic origin. The nucleic acid may, in accordance with the invention also be able to be altered by genetic engineering processes from the wild-type of the nucleic acid, and/or it may contain unnatural and/or unusual nucleic acid building blocks. The nucleic acid may be combined with molecules of other types, for example with proteins.

In conjunction with the present invention, a "protein" is understood to be a molecule that consists of at least two amino acids connected to each other by means of an amide bond. In the context of the present invention, a protein may also be a peptide, for example an oligopeptide, a polypeptide, or, for example, an isolated protein domain. Such a protein may have a natural or synthetic origin. The protein may be modified by means of genetic engineering methods relative to wild-type protein, and/or it may contain unnatural and/or unusual amino acids. The protein may be derivatized relative to the wild-type form, for example it may have glycosyl groups, it can be shortened, it may be fused together with other proteins, or it may be connected with molecules of a certain type, for example with carbohydrates. In accordance with the invention, a protein may, in particular, be an enzyme, a receptor, a cytokine, an antigen, or an antibody.

"Antibody" means a polypeptide that is essentially coded by one or more immunoglobulin genes or fragments thereof that specifically bonds/bond and recognizes/recognize an analyte (antigen). Antibodies occur, for example, as intact immunoglobulins or as a series of fragments that are generated with various peptidases by means of cleavage. "Antibody" also means modified antibodies, for example oligomeric, reduced, oxidized, and marked antibodies. "Antibodies" also comprise antibody fragments that have been produced either by means of the modification of entire antibodies or by means of de-novo synthesis using DNA recombination techniques.

The term "antibody" includes both intact molecules as well as fragments thereof, such as Fab, F(ab)'$_2$, and Fv, which can bind epitope determinants.

In the case of PNA (peptide nucleic acid, or polyamide nucleic acid) molecules, such molecules are not negatively charged, and they function in the same way as DNA (Nielsen et al., 1991, *Science*, 254, 1497-1500; Nielsen et al., 1997, *Biochemistry*, 36, 5072-5077; Weiler et al., 1997, *Nuc. Acids Res.*, 25, 2792-2799). PNA sequences comprise a polyamide basic frame of N-(2-aminoethyl)-glycine units, and they do not possess any glucose units nor any phosphate groups.

In a further embodiment of the invention, the biochip that is manufactured on the biochip platform made using the biochip platform of the invention, in particular on the bottom of the reaction chamber, comprises immobilized or bound biological molecule markers that permit the easy detection of these molecules using suitable detection methods. These markings may, for example, be a fluorescence marking, a UV/VIS marking, a superparamagnetic function, a ferromagnetic function, and/or a radioactive marking. The detection methods used for this marking may, for example, be fluorescence or UV-VIS spectroscopy, waveguide spectroscopy, impedance spectroscopy, and electrical and/or radiometric methods.

In one embodiment of the invention, the same biologically active molecule is immobilized in each reaction chamber of the biochip platform of the invention or of the biochip of the invention. In a further preferred embodiment of the invention, a different molecule is immobilized in each reaction chamber of the biochip platform of the invention or of the biochip of the invention.

In a further preferred embodiment of the invention that relates to a biochip platform as described above, and also to a biochip, said platform has a removable volume-enlarging device, for example one that can be clipped on, that at least comprises one volume-enlarging chamber that is open in the upward and downward directions. The volume-enlarging device may be permanently attached to the biochip platform, for example by means of hinges, but it may also be separate from the biochip platform and not clipped onto its reaction chamber until it is needed, or it may otherwise be attached in a reversible manner. In this more preferred embodiment, the reaction chamber of the biochip platform of the invention, which has at least one reaction chamber, has the reversibly attachable volume-enlarging chamber for the at least one reaction chamber and permits the biochip platform of the invention to have a larger volume for certain steps, for example hybridization or rinsing steps. The height of the side walls of the volume-enlarging chamber is preferably substantially higher, for example 5, 10, 15, 20, 25, 30, 40, 50, 60, 70, 80, 90, or 100 times higher than the height of the side walls of the reaction chamber at the same bottom surface area of the given chamber. If the biochip platform of the invention has more than one reaction chamber, a reversibly attachable volume-enlarging chamber may be provided for each individual one of these multiple or numerous reaction chambers, whereby this plurality of volume-enlarging chambers may also be present in a unit, for example in strip or matrix form, wherein the volume-enlarging chambers are connected to each other by means of the frame part. The volume-enlarging devices thus provided in combination with the biochip carriers of the invention are characterized in a preferred embodiment by the fact that they each have a frame part and side walls that form the volume-enlarging chamber. The side walls enclose on the sides a chamber or volume that is not closed off in the upward or downward directions, but rather is open. The volume-enlarging device, which comprises at least one volume-enlarging chamber and a frame part, essentially serves to increase the height of the side walls of the reaction chamber, which themselves have a low height, in a reversible manner, so that the side walls that form the reaction chamber can be made higher in a reversible manner and the volume that is surrounded by them can be increased. In a more preferred embodiment, the contour of the volume enclosed by the side walls of the volume-enlarging chamber, respectively the surface area of the contour of the surface of the bottom of the volume-enlarging reaction chamber corresponds to the platform plate. If, for example, the reaction chamber of the platform plate has a rectangular or square contour, its side walls are perpendicular to each other and they accordingly enclose a rectangular or square bottom, so that the volume-enlarging chamber also has side walls that are arranged at right angles to each other and that comprise a rectangular or square surface that coincides with the surface of the bottom (seen in contour), whereby the volume or space that is enclosed by the side walls of the volume-enlarging chamber is open in an upward and downward direction, namely toward the reaction chamber.

In an especially preferred embodiment the volume-enlarging device is inserted onto one, more than one, or many reaction chambers associated with it in such a way that a liquid-tight connection is achieved between the side walls of each volume-enlarging chamber and the side walls of each reaction chamber of the platform plate that is associated with a volume-enlarging chamber. This can be accomplished by constructing the volume-enlarging device, in particular its side walls, of an elastic or flexible material that meets the aforesaid requirements. The volume-enlarging device, and respective volume-enlarging chambers, may also be clipped onto or otherwise connected to the associated reaction chambers, however this connection must be reversible in order to permit attachment and removal. The volume-enlarging device can be made, for example, of silicone, of a polymer, for example polyurethane, or of some other liquid-sealing material.

In an especially preferred embodiment the invention relates to a combination of a volume-enlarging device as constructed above that has at least one, for example a plurality or a large number, of volume-enlarging chambers disposed in a frame part that may, for example, be designed as a strip or matrix, and a biochip platform in accordance with the invention. In a preferred embodiment the biochip platform may have at least one reaction chamber located on a base, preferably more than one or a large number of reaction chambers, each disposed on individual bases. This embodiment is especially advantageous in that the respective side walls of the volume-enlarging device that form the volume-enlarging chamber can be reversibly connected to the side walls of the reaction chamber located on the base in an especially easy and especially liquid-tight manner.

In an especially preferred embodiment, a sealing mat (gasket) or sealing matrix is disposed between the biochip platform and the removable volume-enlarging device, and this mat or matrix achieves an improved liquid-tight connection between the biochip platform and the volume-enlarging device. This is achieved in particular because the sealing mat is preferably made from an elastic liquid-tight material, for example a polymeric material, that is equipped with recesses for at least one reaction chamber and that fills in the depressions between adjacent reaction chambers of a biochip platform so that, when the volume-enlarging device is set onto the biochip platform, any leaks and cross-contamination that might possibly occur are prevented.

In a further preferred embodiment, the volume-enlarging chambers of the volume-enlarging device are reversibly closeable, for example by means of a cover associated with the individual chambers.

Of course, the invention also relates to a kit comprising a biochip platform of the invention together with a conventional microtiter plate.

Of course, the invention also relates to a kit comprising a biochip platform of the invention together with a volume-enlarging device as described above.

Of course, the invention also relates to a kit comprising a biochip platform of the invention together with a volume-enlarging device as described above and a sealing mat as described above.

Of course, the invention also relates to a kit comprising a biochip platform of the invention with a volume-enlarging device as described above, optionally together with a sealing mat, optionally together with closing devices, for example covers, for the volume-enlarging chamber, and a conventional microtiter plate.

The present invention also relates to the use of the biochip platform of the invention, or use of the biochip made using the biochip platform of the invention, optionally in combination with a volume-enlarging device, to test an analyte in a sample and/or to isolate it and/or to purify it. In conjunction with the present invention an "analyte" is understood to mean a substance the nature and quantity of whose individual components is to be determined and/or that is to be separated from mixtures. Specifically, the analyte is proteins, nucleic acids, carbohydrates, and similar compounds. In a preferred embodiment of the invention the analyte is a protein, peptide, antigen, or a nucleic acid. A "sample" is understood to mean an aqueous or organic solution, emulsion, dispersion, or suspension that contains the analyte defined above in isolated and in purified form or that contains various substances as components of a complex mixture. A sample may, in particular, be a biological liquid, such as blood, lymphatic fluid, tissue fluid, etc., in other words, a liquid taken from a living or dead organism, organ, or tissue. A sample may already have been subjected to purification steps, but it may also be unpurified.

The present invention, therefore, also relates to the use of the biochip platform of the invention, respectively of a biochip made using the biochip platform of the invention, optionally in combination with a volume-enlarging device, in order to perform analytical and/or detection procedures, which for example may be mass spectroscopy, fluorescence or UV-VIS spectroscopy, fluorescence or light microscopy, wave guide spectroscopy, or an electrical procedure such as impedance spectroscopy.

The present invention also relates to the use of the biochip platform, or use of the biochip made using the biochip platform of the invention, optionally in combination with a volume-enlarging device, to detect and/or isolate biological molecules. For example, a biochip platform or biochip of the invention may be used optionally in combination with a volume-enlarging device that preferably has a single-strand nucleic acid in immobilized form, to detect a complementary nucleic acid in a sample and/or to isolate this complementary nucleic acid. For example, a biochip platform or biochip of the invention may be used optionally in combination with a volume-enlarging device that has a protein in immobilized form to detect and/or to isolate a second protein acid that is present in a sample and that interacts with the immobilized protein.

The present invention also relates to the use of the biochip platform of the invention, or use of the biochip made using the biochip platform, optionally in combination with a volume-enlarging device, to develop pharmaceutical formulations. The present invention also relates to the use of the biochip platform of the invention, or use of the biochip made using the biochip platform of the invention, optionally in combination with a volume-enlarging device, to investigate the effects and/or side effects of pharmaceutical formulations. The biochip platforms of the invention, or the biochips made using the biochip platform of the invention, optionally in combination with a volume-enlarging device, may also be used to diagnose diseases, for example to identify pathogens and/or to identify mutated genes that cause diseases to develop. A further possible use of the biochip platform, or use of the biochips of the invention, optionally in combination with a volume-enlarging device, comprises the investigation of the microbiological contamination of, for example, foods, drinking water, waste water, or fermenters.

Further preferred embodiments of the invention will become apparent from the dependent claims.

BRIEF DESCRIPTION OF THE DRAWINGS

The biochip platform of the invention is explained below on the basis of typical examples and the corresponding figures.

The drawing shows.

DETAILED DESCRIPTION OF THE INVENTION

In the following section, parts, elements, or devices that have similar construction or function have the same reference numbers.

Figure 1:
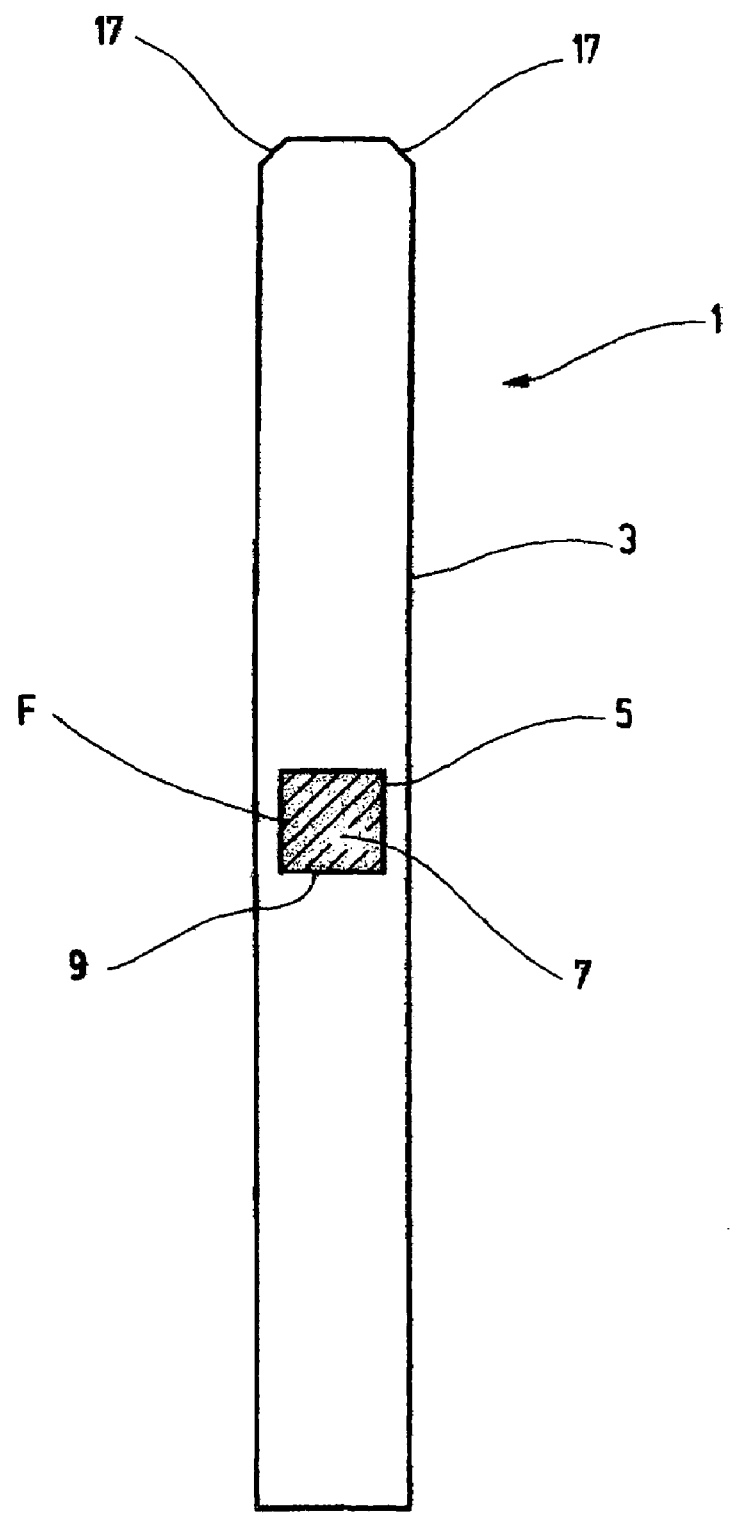
FIG. 1 A schematic diagram of a biochip platform of the invention seen in a top view, FIG. 2 A schematic diagram of two alternative embodiments of the biochip platform of the invention in a cross-sectional view, FIG. 3 A top view of seven alternative embodiments of the biochip platform of the invention, FIG. 4 A side view of two alternative embodiments of the biochip platform of the invention and a microtiter plate with the biochip carriers of the invention inserted, FIG. 5 A side view of another alternative embodiment of the biochip platform of the invention FIG. 6 A side view of two additional preferred embodiments of the biochip platform of the invention, in which the reaction chambers are located on bases, FIG. 7 An embodiment of a volume-enlarging device of the invention in strip form, FIG. 8 A side view of a volume-enlarging device that can be attached to a biochip platform of the invention in SBS format, in which the biochip platform can be attached to a conventional microtiter plate, and FIG. 9 A biochip platform in the SBS format and a volume-enlarging device in SBS format associated therewith, wherein a sealing mat in the SBS format is disposed between these two components.

FIG. 1 shows in schematic form a biochip platform 1 with a rectangular platform plate 3 that in places has keyed corners 17. A reaction chamber 5 that is formed by the bottom 7 having the hatched surface F and the side walls 9 that laterally define or enclose the bottom 7 is located on the platform plate 3. The reaction chamber 5, which has a square contour, is open in the upward direction. The platform plate 3 has two keyed corners 17 that permit the biochip platform 1 to be uniquely oriented, for example when inserted into a microtiter plate.

Figure 2A:
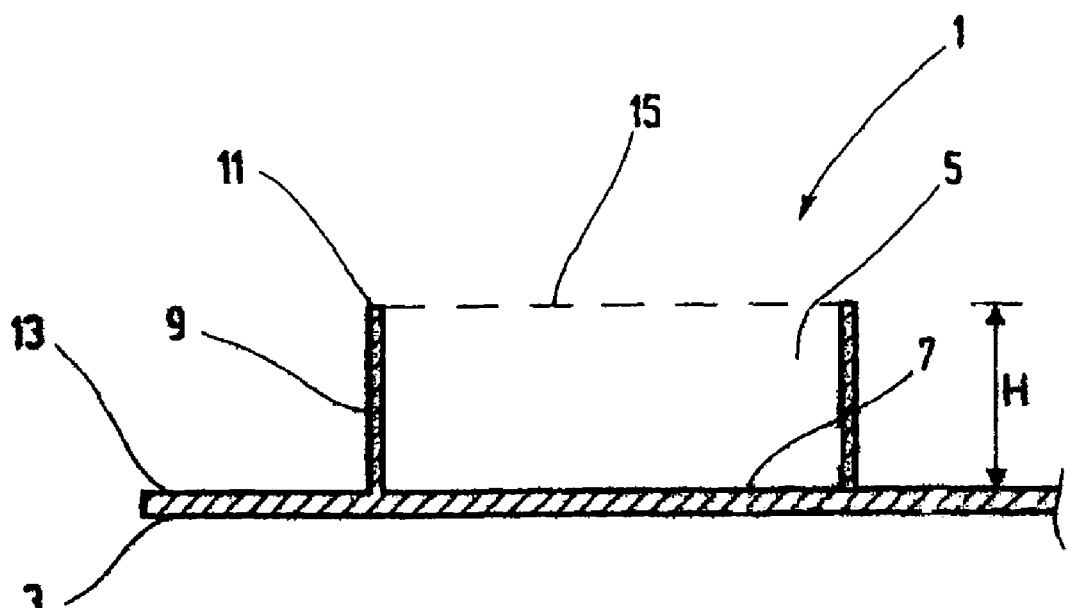
Figure 2B:
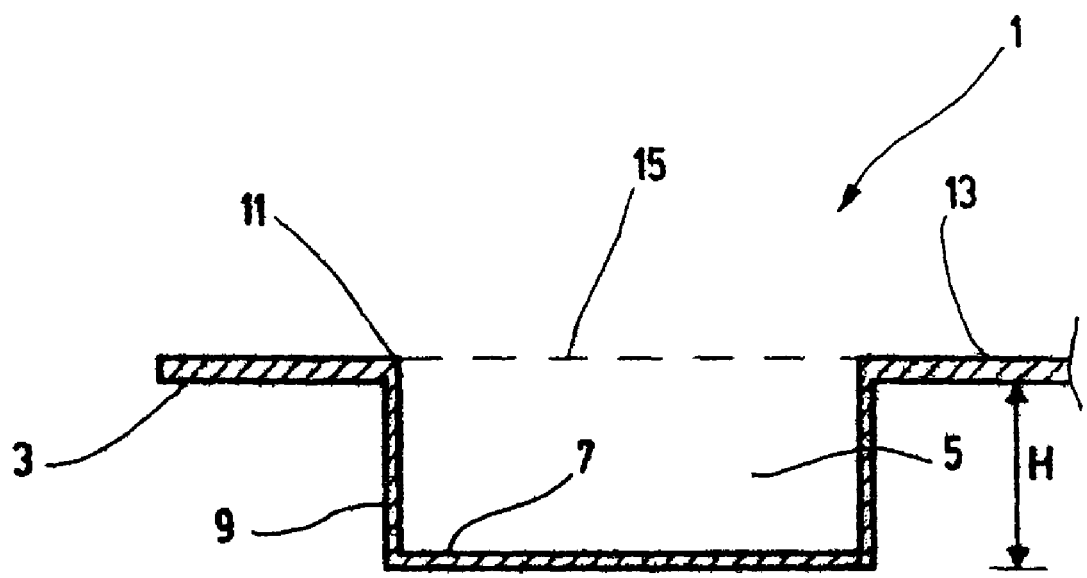

FIG. 2 shows in schematic form a cross section through two alternative embodiments of the biochip platform 1 of the invention. FIG. 2a shows an embodiment of the biochip platform 1 of the invention in which the bottom 7 of the reaction chamber 5 is formed by the platform plate 3. The side walls 9 of the reaction chamber 5 having a height H are formed as raised areas on the platform plate 3. The reaction chamber 5, which is open in the upward direction, has an opening 15. In this embodiment, the upper edge 11 of the reaction chamber 5 lies in a plane above the upper edge 13 of the platform plate 3. FIG. 2b shows an embodiment of the biochip platform 1 of the invention in which the upper edge 11 of the reaction chamber 3 and the upper edge 13 of the platform plate 3 lie in the same plane. In this embodiment the reaction chamber 5 is disposed as a depression inside and/or below the platform plate 3, and the opening 15 of the reaction chamber 5 terminates at the upper edge 13 of the platform plate 3.

FIG. 3 shows a top view of alternative embodiments of the biochip platform 1 of the invention. The biochip platform 1 of the invention is designed in strip form, and the length of the biochip platform 1 permits it to preferably be inserted into a microtiter plate designed according to the SBS standard. The width of the biochip platform 1 is, in each case, 9 mm. The reaction chambers 5 disposed on the platform plate 3 are each open in the upward direction. The respective platform plate 3 of the embodiments shown, in each case has two keyed corners 17 that permit the biochip platform 1 to be uniquely oriented, for example when inserted into a microtiter plate.

Figure 3A:
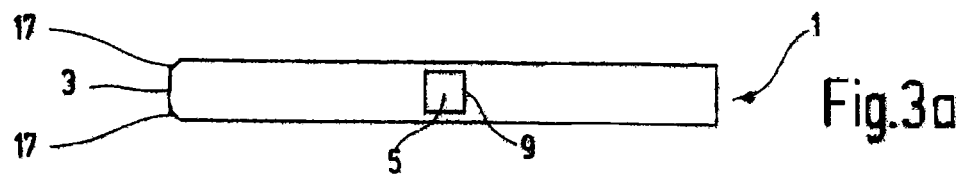

FIG. 3a shows an embodiment in which a reaction chamber 5 is disposed on the platform plate 3 of the biochip platform 1. The reaction chamber 5 has a square contour with a side length of 6 mm. When the height of the side walls 9 of the reaction chamber 5 is 0.6 mm, the ratio of the numerical value of the bottom surface area to the numerical value of the height of the side walls ($36(mm^2):0.6(mm)=60$) is 60. When the height of the side walls 9 of the reaction chamber 5 is 0.5 mm, the ratio of the numerical value of the bottom surface area to the numerical value of the height of the side walls is 72. When the height of the side walls 9 of the reaction chamber 5 is 0.4 mm, the ratio of the numerical value of the bottom surface area to the numerical value of the height of the side walls is 90.

Figure 3B:
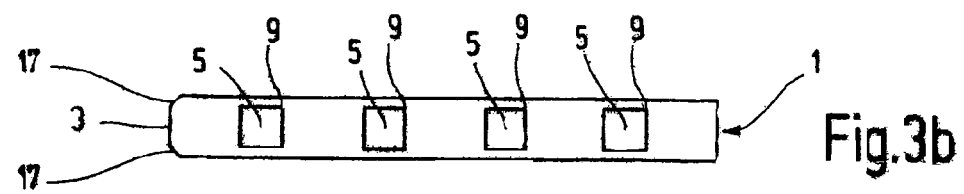

FIG. 3b shows an embodiment in which the four uniformly spaced reaction chambers 5 are located in a row on the platform plate 3 of the biochip platform 1. The four reaction chambers 5 each have a square contour with a side length of 6 mm on each side.

Figure 3C:
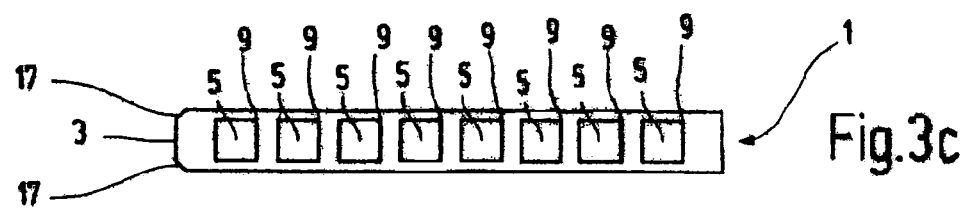

FIG. 3c shows an embodiment in which the eight uniformly spaced reaction chambers 5 are located in a row on the platform plate 3 of the biochip platform 1. The eight reaction chambers 5 each have a square contour with a side length of 6 mm on each side.

Figure 3D:
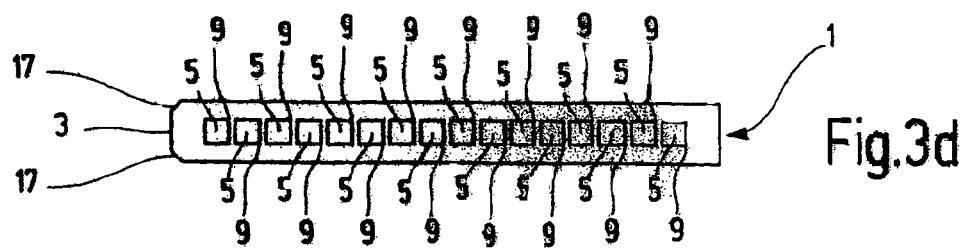

FIG. 3d shows an embodiment in which the sixteen uniformly spaced reaction chambers 5 are located in a row on the platform plate 3 of the biochip platform 1. The sixteen reaction chambers 5 each have a square contour with a side length of 3.5 mm on each side. When the height of the side walls 9 of the reaction chamber 5 is 0.4 mm, the ratio of the numerical value of the base surface area to the numerical value of the height of the side walls is approximately 30. When the height of the side walls 9 of the reaction chamber 5 is 0.3 mm, the ratio of the numerical value of the bottom surface area to the numerical value of the height of the side walls is approximately 40. When the height of the side walls 9 of the reaction chamber 5 is 0.2 mm, the ratio of the numerical value of the bottom surface area to the numerical value of the height of the side walls is approximately 61.

Figure 3E:
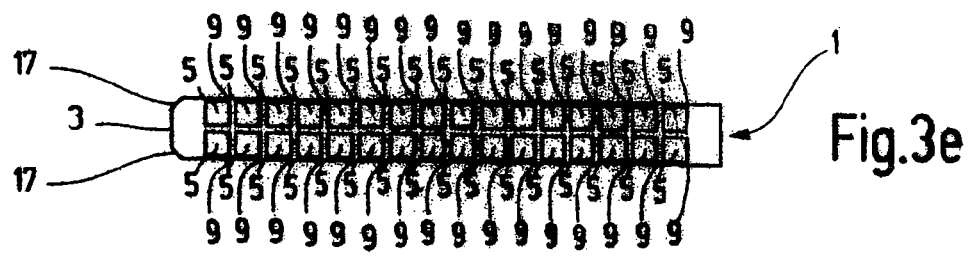

FIG. 3e shows an embodiment in which the thirty-two uniformly spaced reaction chambers 5 are located in two parallel rows on the platform plate 3 of the biochip platform 1. The thirty-two reaction chambers 5 each have a square contour with a side length of 3.5 mm on each side.

Figure 3F:
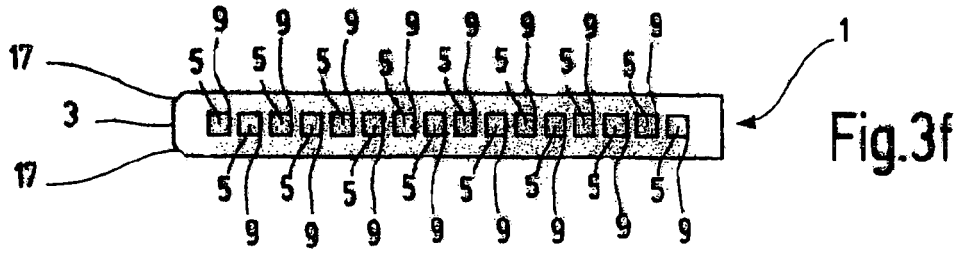

FIG. 3f shows an embodiment in which the sixteen uniformly spaced reaction chambers 5 are located in a row on the platform plate 3 of the biochip platform 1. The sixteen reaction chambers 5 each have a square contour with a side length of 3 mm on each side. When the height of the side walls of the reaction chamber 5 is 0.3 mm, the ratio of the numerical value of the bottom surface area to the numerical value of the height of the side walls is 30. When the height of the side walls 9 of the reaction chamber 5 is 0.2 mm, the ratio of the numerical value of the bottom surface area to the numerical value of the height of the side walls is 45.

Figure 3G:
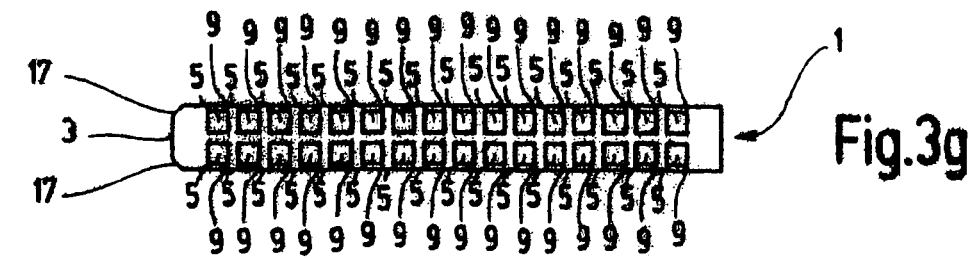

FIG. 3g shows an embodiment in which the thirty-two uniformly spaced reaction chambers 5 are disposed in two parallel rows on the platform plate 3 of the biochip platform 1. The thirty-two reaction chambers 5 each have a square contour with a side length of 3 mm on each side.

FIG. 4 shows a side view of two alternative embodiments of the biochip platform 1 of the invention in which the bottom 7 lies in a plane with the upper edge 17 of the platform surface 3 and of a microtiter plate with the biochip carriers 1 of the invention inserted.

FIG. 4a shows a biochip platform 1 designed in strip form, in which eight uniformly spaced reaction chambers 5 are disposed in a row on the platform plate 3. In this embodiment the upper edge 11 of the reaction chambers 5 formed by the side walls 9, which are designed as raised areas, are in a plane above the upper edge 13 of platform plate 3. The reaction chambers 5, which are open in the upward direction, each have a square contour. The platform plate 3 has two keyed corners 17, which permit the biochip platform 1 to have a unique orientation. A frame element 21 is provided on the lower edge 19 of the platform plate 3; this frame element is formed by a circumferential hollow wall. The inner wall of the frame element 21, which is not shown, can also be connected by ribs, which likewise are not shown. Extending projections 27 are located at the ends 23 and 25 of the frame element 21, and, when the biochip platform 1 is inserted into a microtiter plate, these projections clip into corresponding recesses in the microtiter plate and in this way, working together with the contact surface 49 which abuts the frame of a microtiter plate, fix the biochip platform 1, respectively in the microtiter plate. Two terminal contact surfaces 49 of the platform plate 3 are shown; they permit the platform surface, for example, to contact a conventional microtiter plate.

FIG. 4b shows the biochip platform 1 designed in strip form which also has eight uniformly spaced reaction chambers 5 which are disposed in a row on the platform plate 3, and the reaction chamber 5 is formed by side walls 9 that are designed as raised areas and a bottom 7 lying in the plane of the surface of the platform plate 3. In this embodiment the upper edge 11 of the reaction chambers 5 lies in a single plane above the upper edge 13 of the platform plate 3. In this embodiment the reaction chambers 5, which are open in the upward direction, each have a circular contour. In this embodiment, a frame element 21 formed by a circumferential hollow wall is placed on the lower edge 19 of the platform plate 3. Extending projections 27 are located at the ends 23 and 25 of the frame element 21, and when the biochip platform 1 is inserted into a microtiter plate, these projections clip into corresponding recesses in the microtiter plate and in this way, working together with the contact surface 49 which abuts the frame of a microtiter plate, fix the biochip platform 1 in and onto the microtiter plate.

FIG. 4c shows a conventional microtiter plate 100 into which the biochip carriers 1 shown in FIGS. 4a and 4b are inserted and whose position is perpendicular to the length of the microtiter plate 100. The microchip platform 1 covers the cavities 104 of the microtiter plate 100 in the upward direction and is fixed by the contact surfaces 49 on the frame 102 of the microtiter plate 100.

Figure 5:
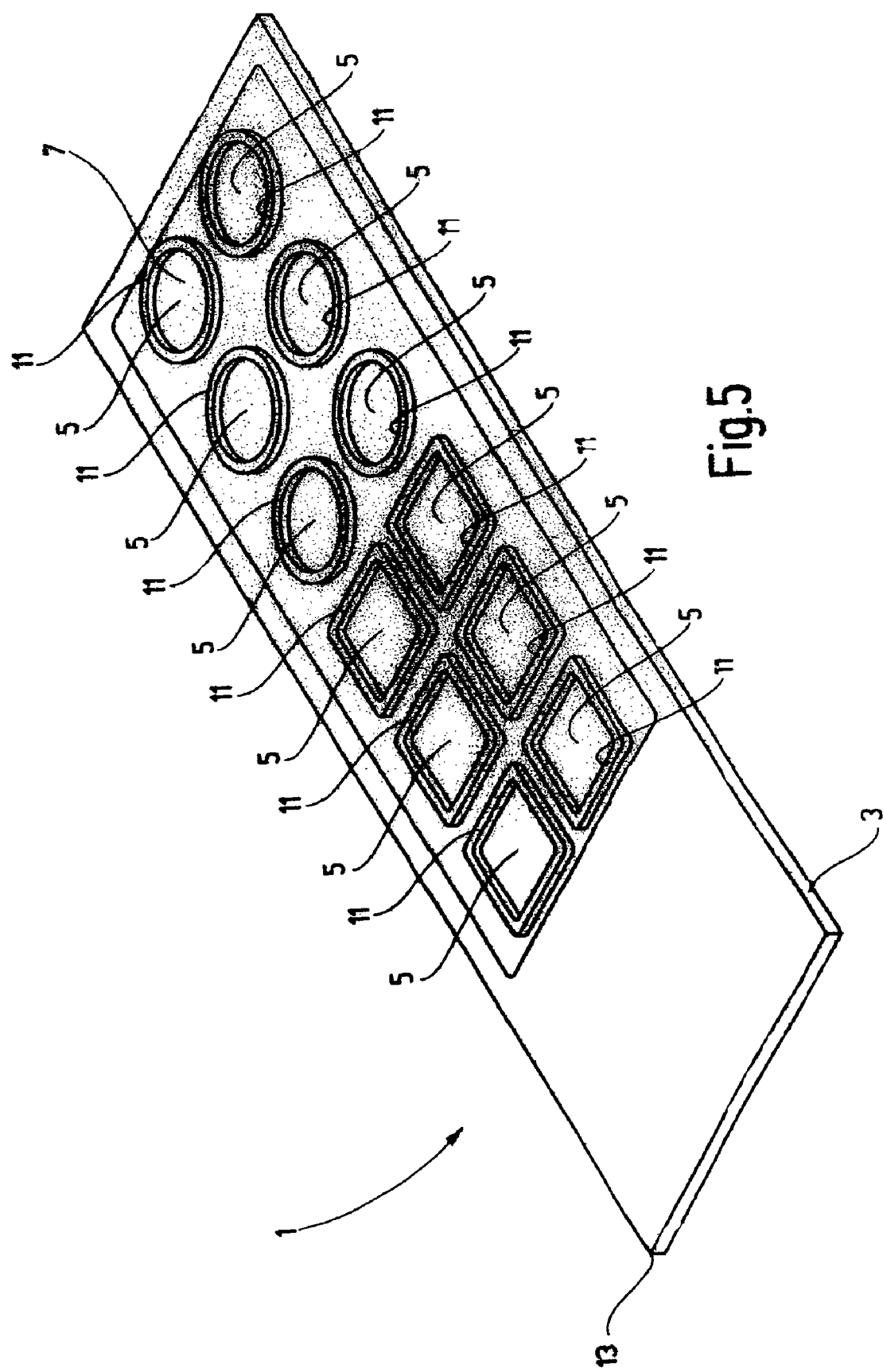

FIG. 5 shows a further embodiment of the biochip platform 1 of the invention. The biochip platform 1 that is shown is configured in the form of a standard microscope slide. Twelve uniformly spaced reaction chambers that are open in the upward direction are arranged in two parallel rows on the platform plate 3. In this embodiment the upper edge 11 of the reaction chambers 5, which are laterally defined by the side walls 9, and which are embodied as raised areas, lies in a plane above the upper edge 13 of the platform plate 3. The bottom 7 lies in a plane with the upper edge 13 of the platform plate 3. Three of the reaction chambers 5 in each of the rows have a circular contour, while the three other reaction chambers 5 in a row have a square contour.

Figure 6A:
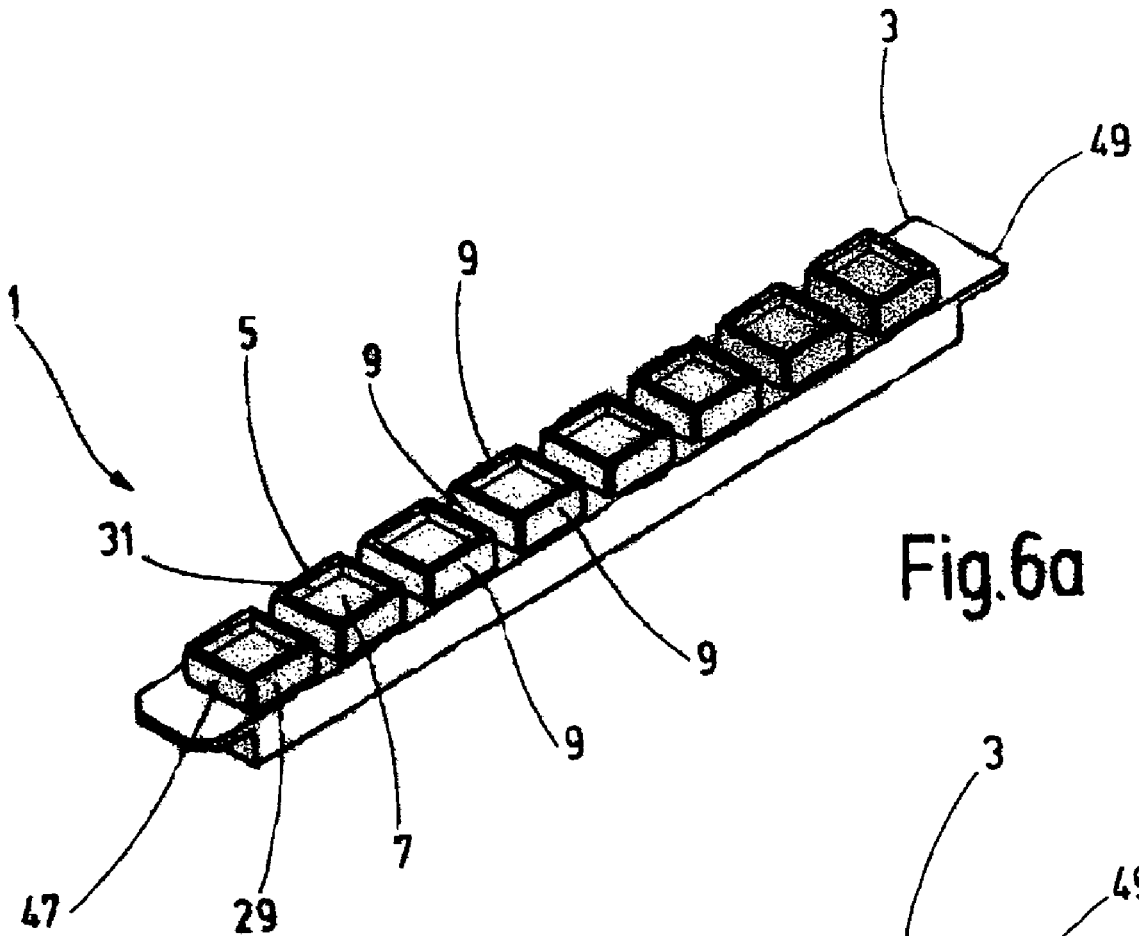

FIG. 6a shows a side view of a biochip platform 1 of the invention, which is designed in strip form and has eight reaction chambers 5 arranged in rows, and the reaction chambers 5 are each constructed with a square contour, and four side walls 9 arranged at right angles to each other, which are embodied as raised areas. These side walls 9, together with the planar bottom 7, which has a square contour, comprise the reaction chambers 5, which are open in the upward direction. The reaction chamber 5 is disposed on a base 29, and the upper surface 31 of the base 29 simultaneously represents the bottom 7 of the reaction chamber 5. Seen in contour, the base 29 has the same geometry and dimensions as the bottom 7 of the reaction chamber 5. The side walls 9 of the reaction chamber 5 simultaneously represent an extension or continuation of the side walls 47 of the base 29 in the same plane. Both the reaction chamber 5 as well as the base 29 are made from the same piece of material and are embodied as an integral component of the platform plate 3.

Figure 6B:
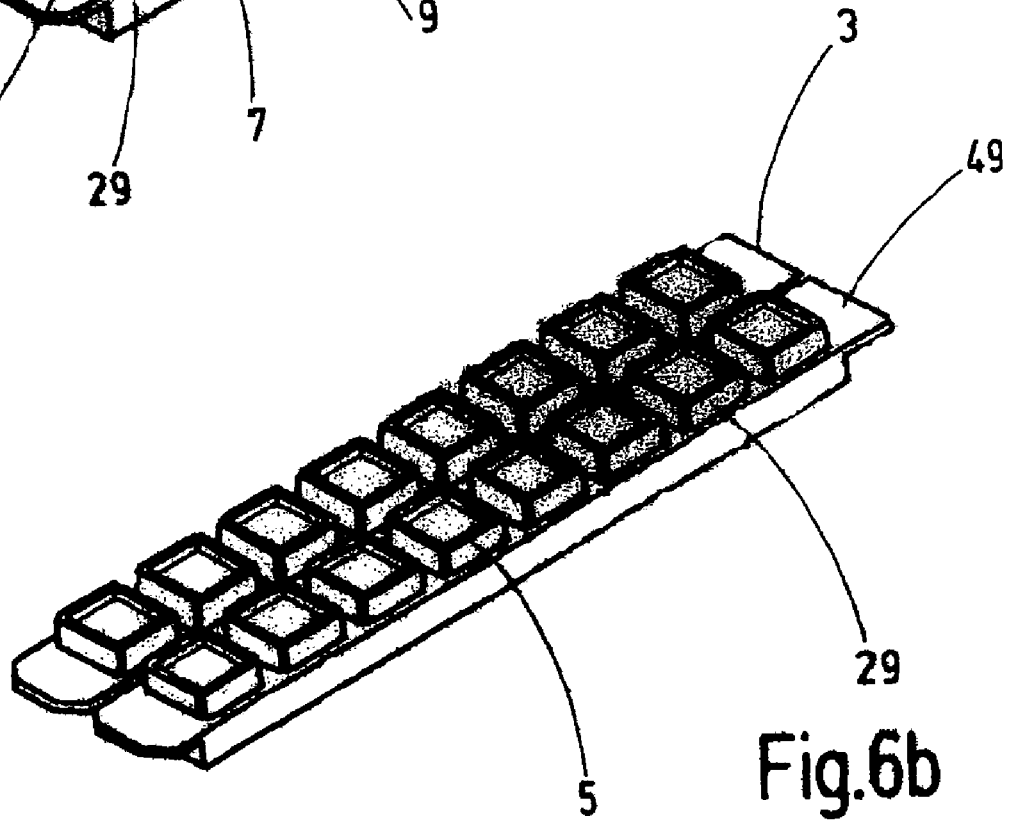

FIG. 6b shows two biochip carriers 1 of FIG. 6a connected to each other. The biochip carriers 1 of FIG. 6a, which are embodied as strips, may be reversibly or permanently connected to each other in accordance to this figure and in this way can be inserted in the form of a 2×8 reaction chamber matrix into a microtiter plate.

Figure 7:
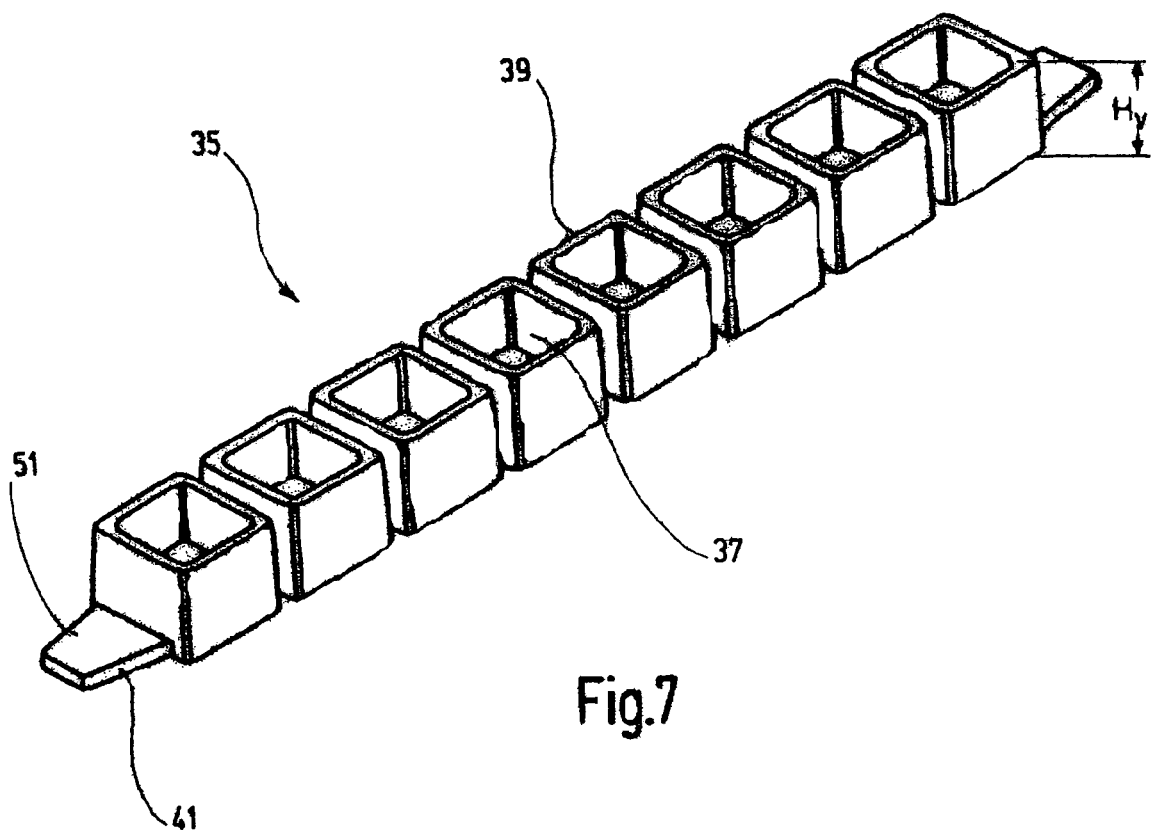

FIG. 7 shows a volume-enlarging device 35 with square volume-enlarging chambers 37 that are arranged sequentially in a row in the form of a strip, and that, when seen in contour, are square. The volume-enlarging chambers are open in the upward and downward (not shown) directions, so that the chambers 37 are formed by each of the four side walls 39, which are arranged at right angles to each other. The height $H_V$ of the side walls 39 is substantially larger than the height H of the side walls 9 of the reaction chamber 5 of a biochip platform of the invention. The frame part 41 that connects the individual volume-enlarging chambers 37 is embodied as a projection 51 on both ends of the strip, and this projection makes it possible to position and fix the volume-enlarging device 35 on a biochip platform 1 of the invention.

Figure 8:
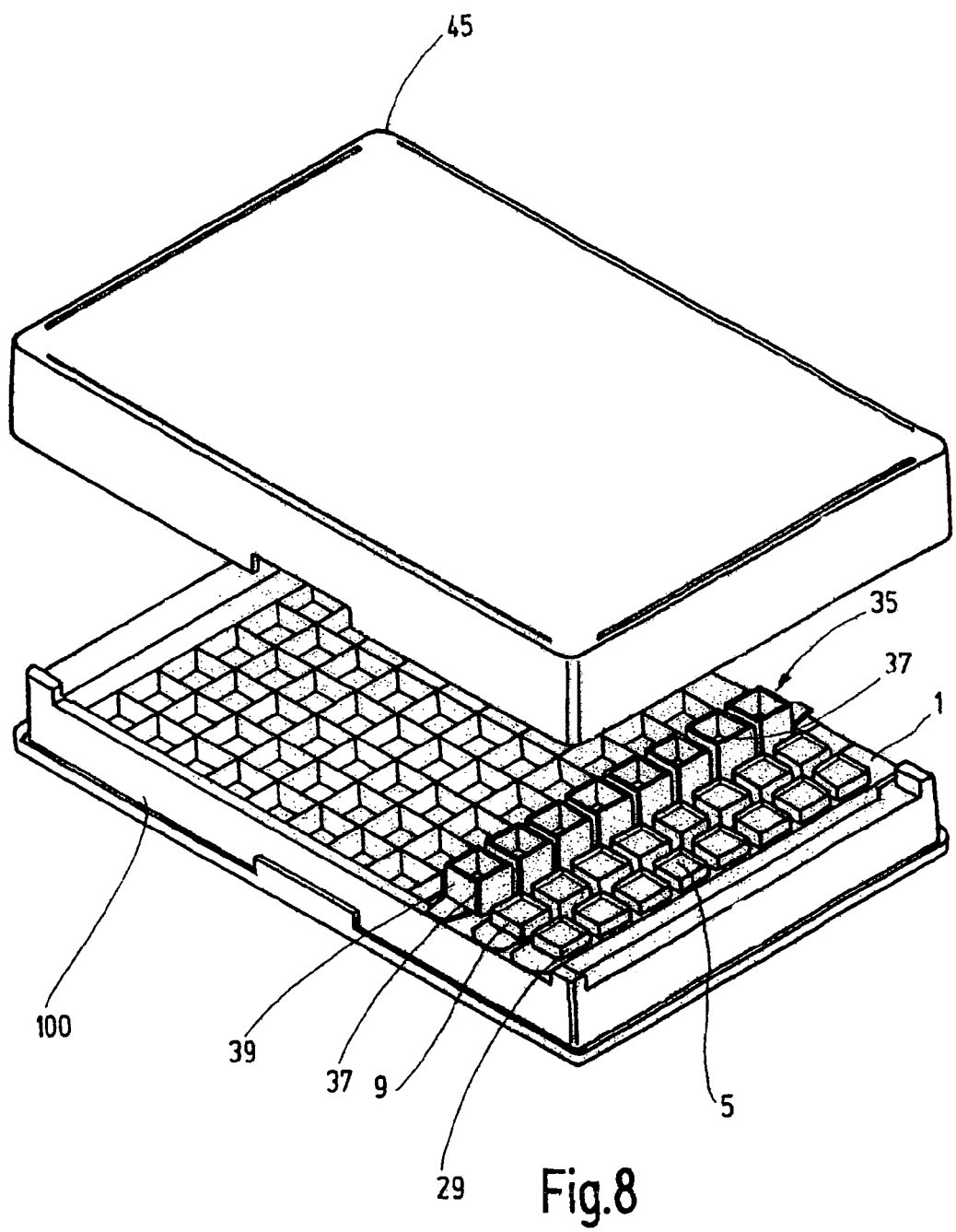

FIG. 8 shows a conventional microtiter plate 100 as well as a biochip platform 1 that can be installed on this plate. The biochip platform 1 is a biochip platform that has reaction chambers 5 disposed on bases 29, as is shown for example in FIGS. 6a and 6b. Also shown is a volume-enlarging device 35 of FIG. 7, which can be reversibly mounted onto the biochip platform 1. When this is done, a volume-enlarging chamber 37 of the volume-enlarging device 35 is associated with each reaction chamber 5 of the biochip platform 1 in such a way that the volume of the reaction chamber 5 essentially increases, in a reversible manner, by the volume of the volume-enlarging chamber 37. This is accomplished by placing the volume-enlarging device 35 onto the biochip platform 1 in such a way that the side walls 39 of the volume-enlarging chambers 37 are fit onto the side walls 9 of the biochip platform 1 in a liquid-tight manner. Also shown is a cover, which can be reversibly installed and which can seal off the upward side of the reaction chamber 5, or the volume-enlarging chamber 37.

FIG. 9 shows a biochip platform 1 of the invention in a matrix form which conforms to the SBS standard. The reaction chambers 5, which are formed from a bottom 7 and side walls 9, which are embodied as raised areas, is shown. Also shown is a volume-enlarging device 35 comprising the 96 volume-enlarging chambers 37 which correlate with the 96 reaction chambers 5 of the biochip platform 1. The dimensions of the volume-enlarging device 35 comprising the 96 volume-enlarging chambers 37 in a frame part 41 correspond to those of a microtiter plate in the SBS format. This volume-enlarging device 35 can be reversibly attached/snapped onto the platform plate of the biochip platform 1, reversibly increasing the respective volume of the reaction chambers 5 of the biochip platform 1, since the individual volume-enlarging chambers 37 are completely open both in the upward and downward directions. In order to improve the liquid seal performance between the reaction chamber 5 of the biochip platform 1 and the volume-enlarging chamber 37, FIG. 9 shows a sealing matrix or sealing mat 43 that can be placed between these two devices. This sealing mat 43, which is preferably made of an elastic, liquid-tight material, for example a polymeric material, is embodied in such a way that it can be placed on the biochip platform 1, and the contours of the reaction chambers 5 are left open and the intermediate areas 53 between reaction chambers 5 are occupied. Accordingly, the sealing mat 43 fits precisely into the recesses 53 between the reaction chambers 5, increasing the seal between the volume-enlarging device 35 and the biochip platform 1. Also shown is a cover 45 that can seal off the reaction chamber 5 and, respectively, the volume-enlarging chamber 37 in an upward direction in a reversibly installable manner. As a general rule: The cover 45 can be associated with individual reaction chambers or with a plurality of reaction chambers, but does not need to cover all of the chambers in the biochip platform.

What is claimed is:

1. A platform for holding chemical, biological or biochemical samples, comprising;
    a base plate having a top surface, a first end, a second end, and a plurality of compartments, said compartments being integrally formed of the same material with said base plate and not a separate piece connected to the base plate;
    said compartments each having a bottom formed by said base plate and a sidewall formed by a raised area on said base plate extending upward from said bottom to an upper edge of said sidewall, there being nothing attached to said upper edge of said sidewall such that the upper edge is the uppermost part of the compartments, said bottom having a width measured in a unit of measure and said sidewall having a height above said bottom to said upper edge measured in said unit of measure, said bottom and said sidewall forming a three-dimensional chamber having an opening in the upward direction;
    wherein the ratio of said width of said bottom to the height of said sidewall is at least 12;
    a first contact surface disposed at said first end of said base plate and extending beyond the perimeter of said compartments and a second contact surface disposed at said second end of said base plate and extending beyond the perimeter of said compartments, said first contact surface and said second contact surface configured to contact a surface of a conventional microtiter plate when said platform is inserted into a conventional microtiter plate;
    at least one projection extending downward from said base plate and configured to clip into a corresponding recess in a conventional microtiter plate; and
    a removable volume enlarging device comprising a plurality of volume enlarging chambers in the form of a strip or a matrix, the volume enlarging chambers each having a volume enlarging chamber sidewall that press fits onto the sidewall of a compartment in a liquid-tight manner, each volume enlarging chamber having an open top and bottom which can be removably placed onto the walls of the compartments to enlarge the height of the sidewalls of the compartments.

2. The platform of claim 1 wherein said ratio of said width of said bottom to said height of said sidewall is greater than 17.5.

3. The platform of claim 1 further comprising a binding area on an internal surface of said compartments for binding at least one chemical entity.

4. The platform of claim 3 wherein said binding area comprises at least one of said bottom or at least a portion of said sidewall.

5. The platform of claim 3 wherein said binding area is formed by functionalizing at least a portion of said internal surface of said compartments.

6. The platform of claim 1 wherein said upper edge of said sidewall is the highest part of the platform when said platform is sitting on said base of said platform.

7. The platform of claim 1 wherein compartments are disposed on a compartment base.

8. The platform of claim 1 wherein said upper edge of said compartments lies in the same plane as said top surface of said base plate.

9. The platform of claim 8 wherein said bottom of said compartments lies below said top surface of said base plate.

10. The platform of claim 1 wherein said bottom of said compartments is in the shape of one of the shapes selected from the group, a circle, rectangle, square, hexagon, polygon, or an ellipse.

11. The platform of claim 1 wherein the base plate is configured to permit said platform to be inserted into a microtiter plate having dimensions in accordance with the SBS (Society of Bimolecular Screening) standard.

12. The platform of claim 11 wherein the number of said compartments is selected from the group consisting of 1, 2, 4, 8, 12, integer multiples of 8, and integer multiples of 12.

13. The platform of claim 1 wherein said bottom of said compartments is made of a material selected from the group, polymer, glass, membrane, or a combination of any of these materials, and said bottom has on its surface at least one functional group that can bind a biologically active molecule.

14. The platform of claim 13 wherein the functional group is applied to the surface of said bottom using a chemical functionalization process.

15. The platform of claim 14 wherein said bottom is made of a polymer that has aromatic substituents and said functional group comprises a chloromethyl group.

16. The platform of claim 1 wherein the height of said chamber sidewall is greater than the height of said sidewall of said compartments.

17. The platform of claim 16 wherein said removable volume-enlarging device, when installed onto said compartments, forms a liquid-tight seal between said sidewall of said compartment and said chamber sidewall.

18. The platform of claim 1 further comprising a sealing gasket disposed between said base plate and said removable volume-enlarging device.

19. A platform for holding chemical, biological or biochemical samples, comprising:
   a base plate having a top surface, a first end, a second end, and a plurality of compartments;
   said compartments being integrally formed of the same material with said base plate and not a separate piece connected to the base plate, said compartments arranged in a rectangular matrix comprising a plurality of rows;
   said compartments having a bottom formed of a material and a sidewall extending upward from said bottom to an upper edge of said sidewall, there being nothing attached to said upper edge of said sidewall such that the upper edge is the uppermost part of the compartments, said bottom having a width measured in a unit of measure and said sidewall having a height above said bottom to said upper edge measured in said unit of measure, said bottom and said sidewall forming a three-dimensional chamber having an opening in the upward direction;
   wherein the ratio of said width of said bottom to the height of said sidewall is at least 12;
   a first contact surface disposed at said first end of said base plate and extending beyond the perimeter of said compartments and a second contact surface disposed at said second end of said base plate and extending beyond the perimeter of said compartments, said first contact surface and said second contact surface configured to contact a surface of a conventional microtiter plate when said platform is inserted into a conventional microtiter plate;
   at least one projection extending downward from said base plate and configured to clip into a corresponding recess in a conventional microtiter plate; and
   a removable volume enlarging device comprising a plurality of volume enlarging chambers in the form of a strip configured to enlarge the volume of one row of said plurality of compartments, the volume enlarging chambers each having a volume enlarging chamber sidewall that press fits onto the sidewall of a compartment in a liquid-tight manner, each volume enlarging chamber having an open top and bottom which can be removably placed onto the walls of the compartments to enlarge the height of the sidewalls of the compartments.

20. The platform of claim 19 wherein said ratio of said width of said bottom to said height of said sidewall is greater than one of the following values, 12 or 17.5.

21. The platform of claim 19 further comprising a binding area on an internal surface of said compartments for binding at least one chemical entity.

22. The platform of claim 21 wherein said binding area comprises at least one of said bottom or at least a portion of said sidewall.

23. The platform of claim 21 wherein said binding area is formed by functionalizing at least a portion of said internal surface of said compartments.

\* \* \* \* \*